(12) United States Patent
Lacampagne et al.

(10) Patent No.: US 9,504,732 B2
(45) Date of Patent: Nov. 29, 2016

(54) METHODS FOR TREATING MYOCARDIAL INFARCTION COMPRISING ADMINISTERING SONIC HEDGEHOG

(71) Applicants: INSERM (INSTITUT NATIONAL DE LA SANTE ET DE LA RECHERCHE MEDICALE), Paris (FR); UNIVERSITE DE MONTPELLIER, Montpellier (FR); ASSISTANCE PUBLIQUE-HOPITAUX DE PARIS, Paris (FR); UNIVERSITE PARIS EST CRETEIL VAL DE MARNE, Creteil (FR); UNIVERSITE D'ANGERS, Angers (FR)

(72) Inventors: Alain Lacampagne, Montpellier (FR); Jerome Thireau, Montpellier (FR); Olivier Cazorla, Montpellier (FR); Jean-Yves Le Guennec, Montpellier (FR); Jeremy Fauconnier, Montpellier (FR); Maria del Carmen Martinez, Angers (FR); Ramaroson Andriantsitohaina, Angers (FR); Bijan Ghaleh-Marzban, Maisons-Alfort (FR); Raffaella Soleti, Angers (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR); ASSISTANCE PUBLIQUE-HOPITAUX DE PARIS, Paris (FR); UNIVERSITE PARIS EST CRETEIL VAL DE MARNE, Creteil (FR)

( * ) Notice: Subject to any disclaimer, the term of this patent is extended or adjusted under 35 U.S.C. 154(b) by 0 days.

(21) Appl. No.: 14/760,494

(22) PCT Filed: Jan. 14, 2014

(86) PCT No.: PCT/EP2014/050533
§ 371 (c)(1),
(2) Date: Jul. 13, 2015

(87) PCT Pub. No.: WO2014/108549
PCT Pub. Date: Jul. 17, 2014

(65) Prior Publication Data
US 2015/0352182 A1 Dec. 10, 2015

(30) Foreign Application Priority Data
Jan. 14, 2013 (EP) .................... 13305029

(51) Int. Cl.
*A61K 38/17* (2006.01)
*A61P 9/06* (2006.01)
*A61P 9/00* (2006.01)
*A61K 9/16* (2006.01)
*A61K 9/00* (2006.01)
*C07K 14/47* (2006.01)

(52) U.S. Cl.
CPC ......... *A61K 38/1709* (2013.01); *A61K 9/0019* (2013.01); *A61K 9/16* (2013.01); *C07K 14/4705* (2013.01)

(58) Field of Classification Search
None
See application file for complete search history.

(56) References Cited

U.S. PATENT DOCUMENTS

| 5,789,543 A * | 8/1998 | Ingham ................ A01K 67/027 424/185.1 |
| 9,249,184 B2 * | 2/2016 | Robbins .................. C07K 7/06 |
| 2012/0244136 A1 | 9/2012 | Robbins et al. |

FOREIGN PATENT DOCUMENTS

| WO | 02/080952 A2 | 10/2002 |
| WO | 2005/028616 A2 | 3/2005 |
| WO | 2007/047882 A2 | 4/2007 |
| WO | 2008/115469 A2 | 9/2008 |

OTHER PUBLICATIONS

Agouni et al (2007. FASEB J. 21: 2735-2741).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Kazutaka et al., "Sonic hedgehog is a critical mediator of erythropoietin-induced cardiac protection in mice", Journal of Clinical Investigation, Jun. 2010, pp. 2016-2029, vol. 120, No. 6.
Roncalli et al., "Sonic Hedgehog-Induced Functional Recovery After Myocardial Infarction is enhanced by AMD3100-Mediated Progenitor-Cell Mobilization", Journal of the American College of Cardiology, Jun. 14, 2011, pp. 2444-2452, vol. 57, No. 24, Elsevier Science Inc, New York, NY.

* cited by examiner

*Primary Examiner* — Zachary Howard
(74) *Attorney, Agent, or Firm* — Whitham, Curtis & Cook, P.C.

(57) ABSTRACT

The present invention relates to methods and pharmaceutical compositions for cardioprotection of subjects who experienced a myocardial infarction. In particular, the present invention relates to a ligand of the sonic hedgehog signaling pathway for use in the cardioprotection of a subject who experienced a myocardial infarction.

16 Claims, 11 Drawing Sheets

A

IR Control

IR N-SHH

IR N-SHH+ Ccl

Figure 1:
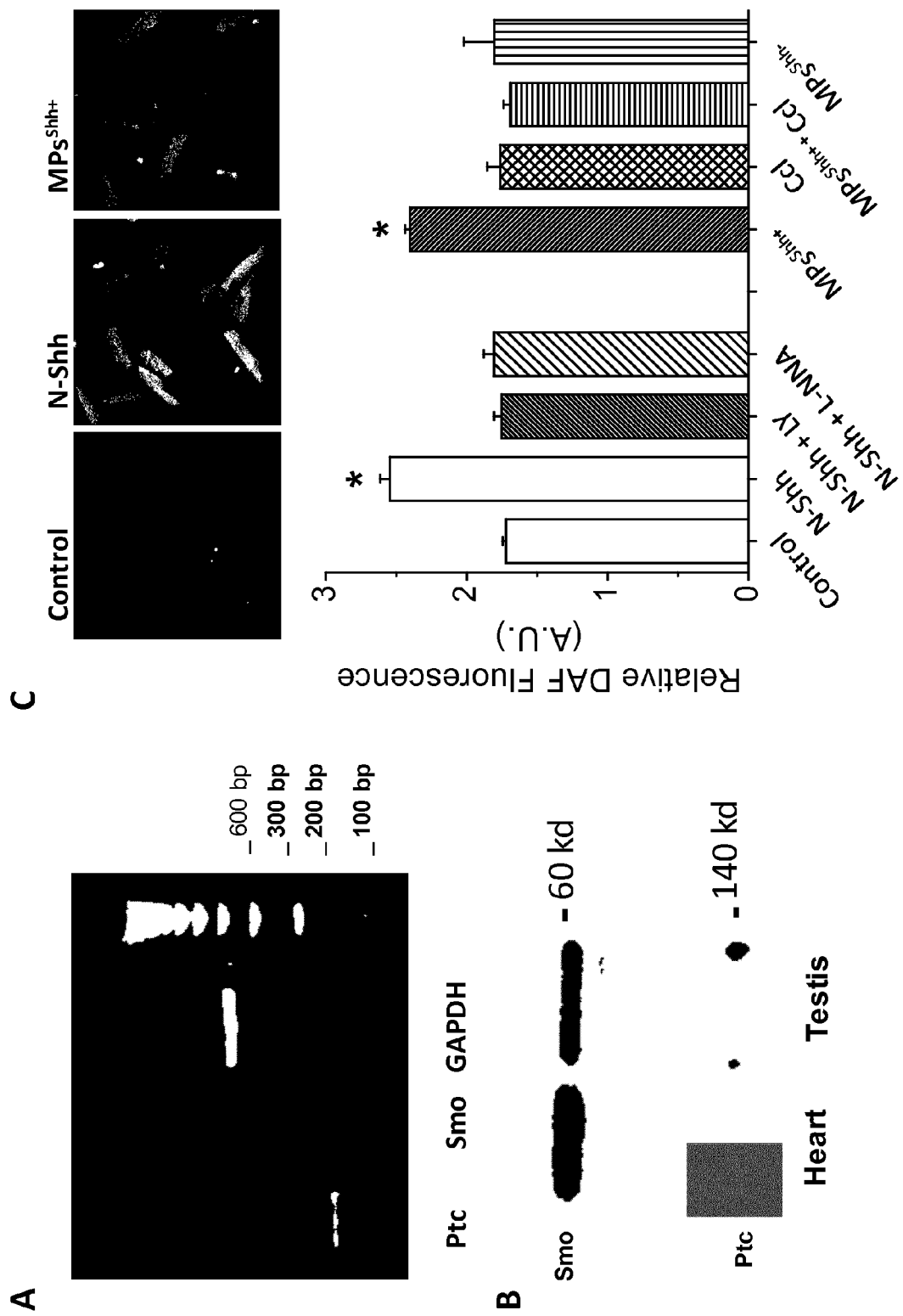

SEQUENCE LISTING

```
<160> NUMBER OF SEQ ID NOS: 1

<210> SEQ ID NO 1
<211> LENGTH: 462
<212> TYPE: PRT
<213> ORGANISM: Homo sapiens

<400> SEQUENCE: 1

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60
```

-continued

```
Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460
```

METHODS FOR TREATING MYOCARDIAL INFARCTION COMPRISING ADMINISTERING SONIC HEDGEHOG

FIELD OF THE INVENTION

The present invention relates to methods and pharmaceutical compositions for cardioprotection of subjects who experienced a myocardial infarction.

BACKGROUND OF THE INVENTION

Myocardial infarction, commonly known as a heart attack, occurs when the blood supply to part of the heart is interrupted causing some heart cells to die. This is most commonly due to occlusion of a coronary artery following the rupture of a vulnerable atherosclerotic plaque. The resulting ischemia and oxygen shortage, if left untreated for a sufficient period of time, can cause damage and or death of heart muscle tissue. Accordingly, in clinical situations of myocardial infarction, the immediate goal is to restore blood flow to the patient as quickly as possible. If blood flow is restored within a suitable time period, tissue damage can be averted. However, a significant delay in restoring blood flow leads to a second condition known as ischemia-reperfusion injury that can develop gradually after an ischemic event and may cause irreversible damage to tissues. Clinical examples include cardiac contractile dysfunction, arrhythmias and irreversible myocyte damage (heart cell death) following myocardial infarction. Accordingly, several methods for the cardioprotection after myocardial infarction have been investigated. For example, current therapies aimed at improving contractile function often involve the use of inotropic agents (e.g., calcium, dopamine, epinephrine, ephedrine, phenylephrine, dobutamine). However inotropic drugs have been reportedly associated with increases in intracellular calcium concentration and heart rate, which may be potentially harmful, especially in hearts with impaired energy balance. Thus the limited successful for cardioprotection is limited by a relatively small number of therapeutic targets. The present invention fulfills this need by providing a new therapeutic target for the cardioprotection after myocardial infarction.

SUMMARY OF THE INVENTION

The present invention relates to a ligand of the sonic hedgehog (Shh) signaling pathway for use in the cardioprotection of a subject who experienced a myocardial infarction.

DETAILED DESCRIPTION OF THE INVENTION

The inventors showed, in physiological situation, in adult cardiomyocytes that sonic hedgehog using either ligand or delivered microparticles can induce a compartmentalized nitric oxide (NO) production, with subsequent activation of a glibenclamide-sensitive inward rectifier potassium channel, i.e. ATP-dependent potassium current (IKATP) resulting in a reduced action potential duration, $Ca^{2+}$ transient amplitude and cell contraction. These effects are mediated through the activation of the Patched-Smoothened complex, PI3-kinase/Akt, NO-synthase and cGMP accumulation. These effects are mimicked by sonic hedgehog carried by lymphocyte-derived shed membrane microparticles, suggesting that microparticles might act in vivo as vectors of a biological message. The in vivo results obtained by the inventors show reduction in QT interval of ECG directly linked to ventricular sonic hedgehog-induced IKATP. In an animal model of ischemia/reperfusion, the administration of sonic hedgehog prior to the reperfusion prevents the enlargement of QT interval. QT prolongation is correlated with ventricular arrhythmias and with sudden cardiac death. Furthermore, activation of sonic hedgehog signaling pathway at the reperfusion prevents lesion of reperfusion at 24 h post reperfusion by a direct mechanism on the myocardium. In conclusion, besides its effect on both angiogenesis and endothelial dysfunction the inventors demonstrate here a novel cardio-protective effect of Shh acting directly on the cardiomyocytes. This study emphasizes the pleotropic effect of Shh pathway as a potential therapeutic target to prevent reperfusion injuries following acute myocardial infarction.

Accordingly, the present invention relates to a ligand of the sonic hedgehog-signaling pathway for use in the cardioprotection of a subject who experienced a myocardial infarction.

As used herein the term "cardioprotection" means protecting against or reducing damage to the myocardium after a myocardial infarction, after, during or prior to ischemic reperfusion. In particular, cardioprotection includes reducing infarct size, reducing reperfusion injuries, preventing QT enlargement (i.e. reducing QT interval), reducing arrhythmias (e.g. ventricular arrhythmias) and improving ventricular repolarization in the context of an ischemic reperfusion. The present invention is thus particularly suitable for reducing the risk of sudden cardiac death after acute myocardial infarction.

A used herein the term "sonic hedgehog signaling pathway", "refers to the chain of events mediated by sonic hedgehog in a cell, in particular in the cardiomyocytes. The sonic hedgehog signaling pathway can be activated, by activating a downstream component, even in the absence of sonic hedgehog protein.

Accordingly the term "ligand of the sonic hedgehog signalling pathway" refers to any compounds, natural or not, capable of mimicking the effect of sonic hedgehog protein in the adult cardiomyocyte. Preferably, the ligand is a compound capable of activating the Patched-Smooth complex in the adult cardiomyocyte or capable of activating IKATP in the adult cardiomyocyte. Typically, the ligand is a peptide, a polypeptide, an antibody, an aptamer or a small organic molecule.

In a particular embodiment, the ligand of the sonic hedgehog signaling pathway is a sonic hedgehog polypeptide.

The term "sonic hedgehog" has its general meaning in the art and refers to the sonic hedgehog protein. The protein is made as a precursor that is auto catalytically cleaved; the N-terminal portion is soluble and contains the signaling activity while the C-terminal portion is involved in precursor processing. More importantly, the C-terminal product covalently attaches a cholesterol moiety to the N-terminal product, restricting the N-terminal product to the cell surface. The term "sonic hedgehog" includes naturally occurring sonic hedgehog and function conservative variants and modified forms thereof. The sonic hedgehog can be from any source, but typically is a mammalian (e.g., human and non-human primate) sonic hedgehog, and more particularly a human sonic hedgehog. The sequence of sonic hedgehog protein and nucleic acids for encoding such proteins are well known to those of skill in the art. For example, Genbank Acc. Nos. AAA62179 (SEQ ID NO:1) provides the complete amino acid sequence of Homo sapiens sonic hedgehog.

However, it should be understood that, as those of skill in the art are aware of the sequence of these molecules, any sonic hedgehog protein or gene sequence variant may be used as long as it has the properties of a sonic hedgehog.

"Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

According to the invention the term "sonic hedgehog polypeptide" refers to any polypeptide that comprises the signalling domain of the sonic hedgehog protein. Accordingly, the term encompasses sonic hedgehog itself or fragments thereof comprising the signalling domain of the hedgehog protein. Preferably the sonic hedgehog polypeptide is a soluble polypeptide and does not comprise the C-amino terminal domain. The signaling domain of the hedgehog protein is the amino terminal domain. As used herein, "amino terminal domain" is an amino acid sequence derived from amino terminal amino acids of the sonic hedgehog protein and having at its carboxy terminus, a glycine-cysteine-phenylalanine (GlyCys-Phe) cleavage site specifically recognized by a proteolytic activity of the carboxy terminal fragment of the native sonic hedgehog polypeptide. In some embodiments, the sonic hedgehog polypeptide comprises the sequence ranging from the amino acid residue at position 1 to the amino acid residue at position 197 in SEQ ID NO:1 or a function conservative variant of said sequence (e.g. a sequence having at least 90% (i.e. 90, 91, 92, 93, 94, 95, 96, 97, 98 or 99%) of identity with the sequence the sequence ranging from the amino acid residue at position 1 to the amino acid residue at position 197 in SEQ ID NO:1).

In specific embodiments, it is contemplated that sonic hedgehog polypeptides used in the therapeutic methods of the present invention may be modified in order to improve their therapeutic efficacy. Such modification of therapeutic compounds may be used to decrease toxicity, increase circulatory time, or modify bio distribution. For example, the toxicity of potentially important therapeutic compounds can be decreased significantly by combination with a variety of drug carrier vehicles that modify bio distribution.

A strategy for improving drug viability is the utilization of water-soluble polymers. Various water-soluble polymers have been shown to modify bio distribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and bio distribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of bio distribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the sonic hedgehog polypeptides described herein for therapeutic delivery.

In a particular embodiment, the sonic hedgehog polypeptide is fused to a Fc portion of an antibody. As used herein, "Fc portion" encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes.

According to the invention, sonic hedgehog polypeptides may be produced by conventional automated peptide synthesis methods or by recombinant expression. General principles for designing and making proteins are well known to those of skill in the art.

Sonic hedgehog polypeptides of the invention may be synthesized in solution or on a solid support in accordance with conventional techniques. Various automatic synthesizers are commercially available and can be used in accordance with known protocols. Sonic hedgehog polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Those of skill in the art are aware of various techniques for optimizing mammalian expression of proteins. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the sonic hedgehog polypeptides of the invention, it would be necessary to employ vectors comprising polynucleotide molecules for encoding the sonic hedgehog-derived proteins. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences, which control transcription and translation. The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed. The choice of a suitable expression vector for expression of the peptides or polypeptides of the invention will of course depend upon the specific host cell to be used, and is within the skill of the ordinary artisan. In general, the vectors useful in the invention include, but are not limited to, plasmids, phagemids, viruses, other vehicles derived from viral or bacterial sources that have been manipulated by the insertion or incorporation of the polypeptides sequences.

Another strategy to produce ligand for sonic hedgehog is the use of shed membrane microparticles. Cells can communicate with other cells through release of microparticles. Microparticles are small vesicles released from stimulated and/or apoptotic cells. They harbor membrane proteins that are characteristic of the original parent cell and intracellular components involved in cell signaling. Microparticles are considered to be both biomarkers and effectors of cell signaling that maintain and/or initiate cell dysfunction. Some types of microparticles possess therapeutic potential through the modulation of cellular processes and of secretomes (the molecules secreted by cells), and subsequently by inducing tissue repair after the reprogramming of target cells. Micorparticles can be engineered to over-express different proteins by driving the synthesis of the relevant such as sonic hedgehog in microparticle-producing cells.

Thus, in particular embodiment, the present invention relates to use of microparticles bearing sonic hedgehog for the cardioprotection of a subject who experienced a myocardial infarction. As the carrier to deliver drugs, microparticles have unique advantages: first, microparticles are formed from cellular membranes, making them therefore much safer and self-friendlier; second, engineering microparticles bearing sonic hedgehog are simple and easily manipulated; and is a general process and not restricted by physicochemical properties of drugs. The use of microparticles promises simple effective carrier of sonic hedgehog and innocuous therapeutic interventions.

In a further object, the present invention relates to a method for treating myocardial infarction in a patient in need thereof comprising the steps consisting of:
i) Restoring blood supply in the cardiac ischemic tissue
ii) Inducing cardioprotection by administrating said patient with therapeutically effective amount of a ligand of the sonic hedgehog signaling pathway according to the invention (e.g., a sonic hedgehog polypeptide or sonic hedgehog carried by microparticles).

By a "therapeutically effective amount" is meant a sufficient amount of the ligand of the sonic hedgehog signaling pathway according to the invention to induce cardioprotection at a reasonable benefit/risk ratio applicable to any medical treatment. It will be understood that the total usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the ligand employed; and like factors well known in the medical arts. For example, it is well known within the skill of the art to start doses of the compound at levels lower than those required to achieve the desired therapeutic effect and to gradually increase the dosage until the desired effect is achieved.

In particular embodiment, steps i) and ii) as above described may performed sequentially or concomitantly. Accordingly, the method of the invention comprises the steps of administering the subject prior to and/or at the time of reperfusion injury with a therapeutically effective amount of a ligand of the sonic hedgehog signaling pathway according to the invention. Typically, the ligand of the sonic hedgehog signaling pathway is administered by infusion into the bloodstream. A second administration may be considered a short time (i.e. 24 hours) after reperfusion.

The ligand of the sonic hedgehog signaling pathway may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The sonic hedgehog polypeptide can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The present invention also relates to the use of a ligand of the sonic hedgehog signaling pathway according to the invention for the preparation of biomaterials or medical delivery devices selected among endovascular prostheses, such as stents, bypass grafts, internal patches around the vascular tube, external patches around the vascular tube, vascular cuff, and angioplasty catheter.

In this respect, the invention relates more particularly to biomaterials or medical delivery devices as mentioned above, coated with such sonic hedgehog polypeptide (or nucleic acid encoding for a sonic hedgehog polypeptide or a vector comprising a nucleic acid encoding for a sonic hedgehog polypeptide) expression and/or activity as defined above, said biomaterials or medical devices being selected among endovascular prostheses, such as stents, bypass grafts, internal patches around the vascular tube, external patches around the vascular tube, vascular cuff, and angioplasty catheter. Such a local biomaterial or medical delivery device can be used to reduce stenosis as an adjunct to revascularizing, bypass or grafting procedures performed in any vascular location including coronary arteries, carotid arteries, renal arteries, peripheral arteries, cerebral arteries or any other arterial or venous location, to reduce anastomic stenosis such as in the case of arterial-venous dialysis access with or without polytetrafluoro-ethylene grafting and with or without stenting, or in conjunction with any other heart or transplantation procedures, or congenital vascular interventions.

For illustration purpose, such endovascular prostheses and methods for coating sonic hedgehog polypetides thereto are more particularly described in WO2005094916, or are those currently used in the art. The compounds used for the coating of the prostheses should preferentially permit a controlled release of said inhibitor. Said compounds could be polymers (such as sutures, polycarbonate, Hydron, and Elvax), biopolymers/biomatrices (such as alginate, fucans, collagen-based matrices, heparan sulfate) or synthetic compounds such as synthetic heparan sulfate-like molecules or combinations thereof. Other examples of polymeric materials may include biocompatible degradable materials, e.g. lactone-based polyesters orcopolyesters, e.g. polylactide; polylactide-glycolide; polycaprolactone-glycolide; poly-orthoesters; polyanhydrides; polyaminoacids; polysaccharides; polyphospha-zenes; poly (ether-ester) copolymers, e.g. PEO-PLLA, or mixtures thereof; and biocompatible non-degrading materials, e.g. polydimethylsiloxane; poly (ethylene-vinylacetate); acrylate based polymers or copolymers, e.g. polybutylmethacrylate, poly (hydroxyethyl methyl-methacrylate); polyvinyl pyrrolidinone; fluorinated polymers such as polytetrafluorethylene; cellulose esters. When a polymeric matrix is used, it may comprise 2 layers, e.g. a base layer in which said inhibitor is incorporated, such as ethylene-co-vinylacetate and polybutylmethacrylate, and a topcoat, such as polybutylmethacrylate, which acts as a diffusion-control of said inhibitor. Alternatively, said inhibitor may be comprised in the base layer and the adjunct may be incorporated in the outlayer, or vice versa.

Such biomaterial or medical delivery device may be biodegradable or may be made of metal or alloy, e.g. Ni and Ti, or another stable substance when intended for permanent use. The inhibitor of the invention may also be entrapped into the metal of the stent or graft body, which has been modified to contain micropores or channels. Also internal patches around the vascular tube, external patches around the vascular tube, or vascular cuff made of polymer or other biocompatible materials as disclosed above that contain the inhibitor of the invention may also be used for local delivery.

Said biomaterial or medical delivery devices allow the inhibitor releasing from said biomaterial or medical delivery devices over time and entering the surrounding tissue. Said releasing may occur during 1 month to 1 year. The local delivery according to the present invention allows for high concentration of the inhibitor of the invention at the disease site with low concentration of circulating compound. The amount of said inhibitor used for such local delivery applications will vary depending on the compounds used, the condition to be treated and the desired effect. For purposes of the invention, a therapeutically effective amount will be administered.

The local administration of said biomaterial or medical delivery device preferably takes place at or near the vascular lesions sites. The administration may be by one or more of the following routes: via catheter or other intravascular delivery system, intranasal, intrabronchial, intraperitoneal or oesophageal. Stents are commonly used as a tubular structure left inside the lumen of a duct to relieve an obstruction. They may be inserted into the duct lumen in a non-expanded form and are then expanded autonomously (self-expanding stents) or with the aid of a second device in situ, e.g. a catheter-mounted angioplasty balloon which is inflated within the stenosed vessel or body passageway in order to shear and disrupt the obstructions associated with the wall components of the vessel and to obtain an enlarged lumen.

The invention will be further illustrated by the following figures and examples. However, these examples and figures should not be interpreted in any way as limiting the scope of the present invention.

FIGURES

FIG. 1: Sonic hedgehog (Shh) receptor complex mediates NO production in ventricular cardiomyocytes. A) Representative PCR gel demonstrating the expression of Patched (Ptc) and Smoothened (Smo) and reference Glyceraldehyde 3-phosphate dehydrogenase (GAPDH) mRNAs in rat ventricular cardiomyocytes. B) Representative Western blot (SDS-page) demonstrating the expression of Smo and Ptc proteins in cardiomyocytes and in testis used as reference tissue. C) Representative confocal images demonstrating the increase in NO production after incubation of cardiomyocytes with recombinant Shh protein (N-Shh) or microparticles harboring the Shh protein ($MPs^{Shh+}$) for 4 h (upper panel). DAF fluorescence levels (lower panel) was quantified in control (n=895 cells), after incubation with N-Shh (n=365 cells), and after co-incubation with phosphoinositide-3 kinase inhibitor, LY294002 (LY, 25 µM, n=98 cells), NOS inhibitor, $N^{\omega}$-nitro-L-arginine (L-NNA, 100 µM, n=98 cells). DAF fluorescence level was also quantified after incubation with $MPs^{Shh+}$ (n=382 cells) and after co-incubation with the Shh pathway inhibitor cyclopamine ($MPs^{Shh+}$-Ccl, 30 µM, n=137 cells). The PTC/Smo inhibitor, Cyclopamine (Ccl, 30 µM, n=68 cells) alone had no effect on basal NO levels. Incubation with MPs not carrying the Shh ($MPs^{Shh-}$) did not enhance NO formation (n=23 cells). Data are mean±SEM; *, p<0.05 vs. control.

Figure 2:
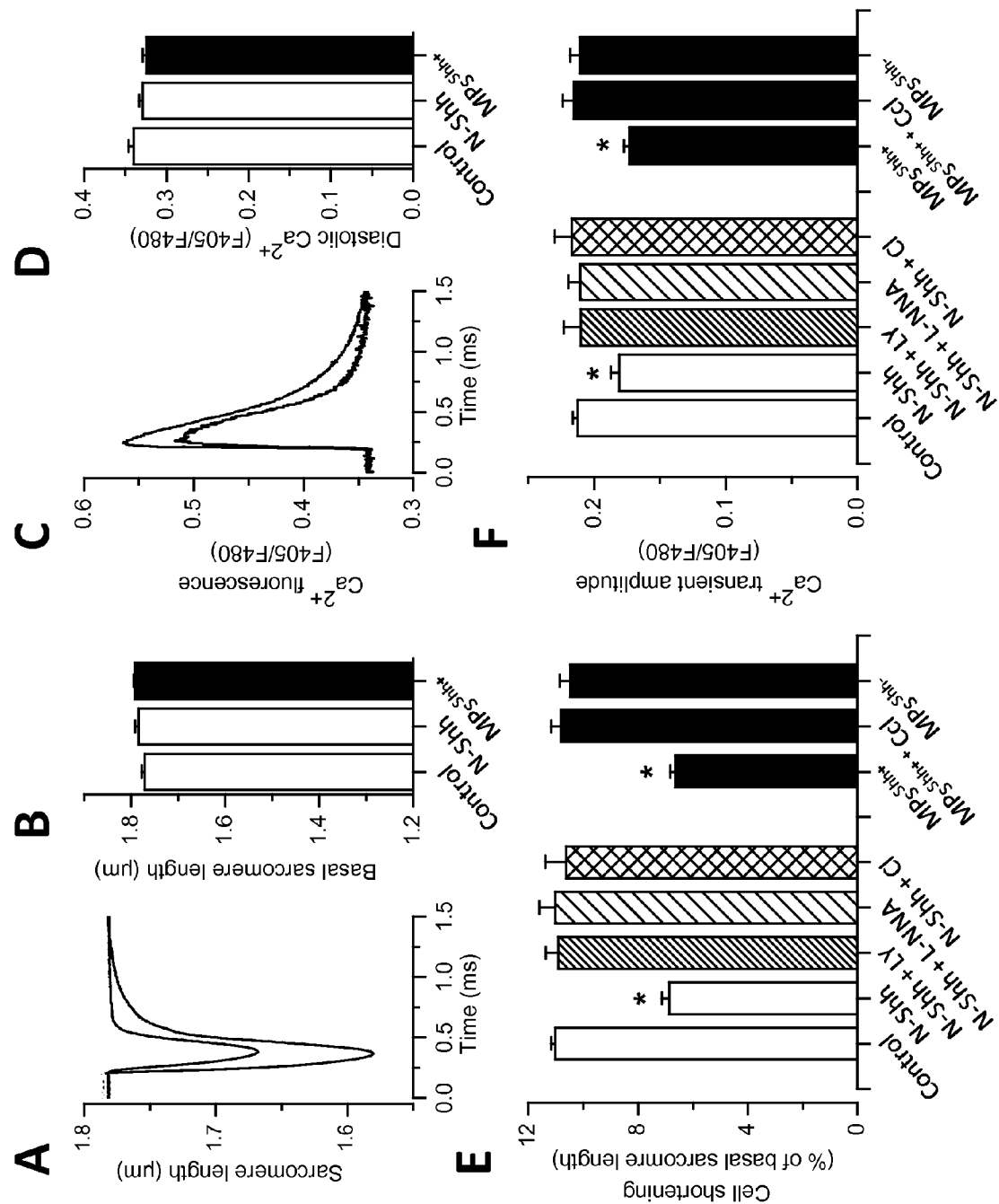

FIG. 2: Shh signal pathway inhibits excitation-contraction coupling of ventricular cardiomyocytes. A) Representative time course of sarcomere length of control, N-Shh-treated and $MPs^{Shh+}$-treated cardiomyocytes. B) Resting sarcomere length in control, N-Shh-treated and $MPs^{Shh+}$-treated cardiomyocytes. C) Representative time-course of $Ca^{2+}$ transient (405/480 nm indo-1 fluorescence) of control cardiomyocytes and cardiomyocytes incubated with a recombinant Shh (N-Shh) or Shh-harboring MPs ($MPs^{Shh+}$) for 4 h. D) Diastolic $Ca^{2+}$ levels in control, N-Shh-treated and $MPs^{Shh+}$-treated cardiomyocytes. Shortening (% of resting sarcomere length) (E) and $Ca^{2+}$ transient amplitude (F) were measured in control (n=253), N-Shh-treated (n=82) or $MPs^{Shh+}$-treated (n=218) cardiomyocytes after incubation with phosphoinositide-3 kinase inhibitor, LY294002 (LY, 25 µM, n=19), NOS inhibitor, $N^{\omega}$-nitro-L-arginine (L-NNA, 100 µM, n=19) and Shh pathway inhibitor, cyclopamine (Ccl, 30 µM, n=17 with N-Shh and n=75 with $MPs^{Shh+}$). Incubation with MPs not carrying the Shh protein ($MPs^{Shh-}$, n=25) did not modify the shortening or $Ca^{2+}$ transient. Data are mean±SEM, *, p<0.05 vs. control.

Figure 3:
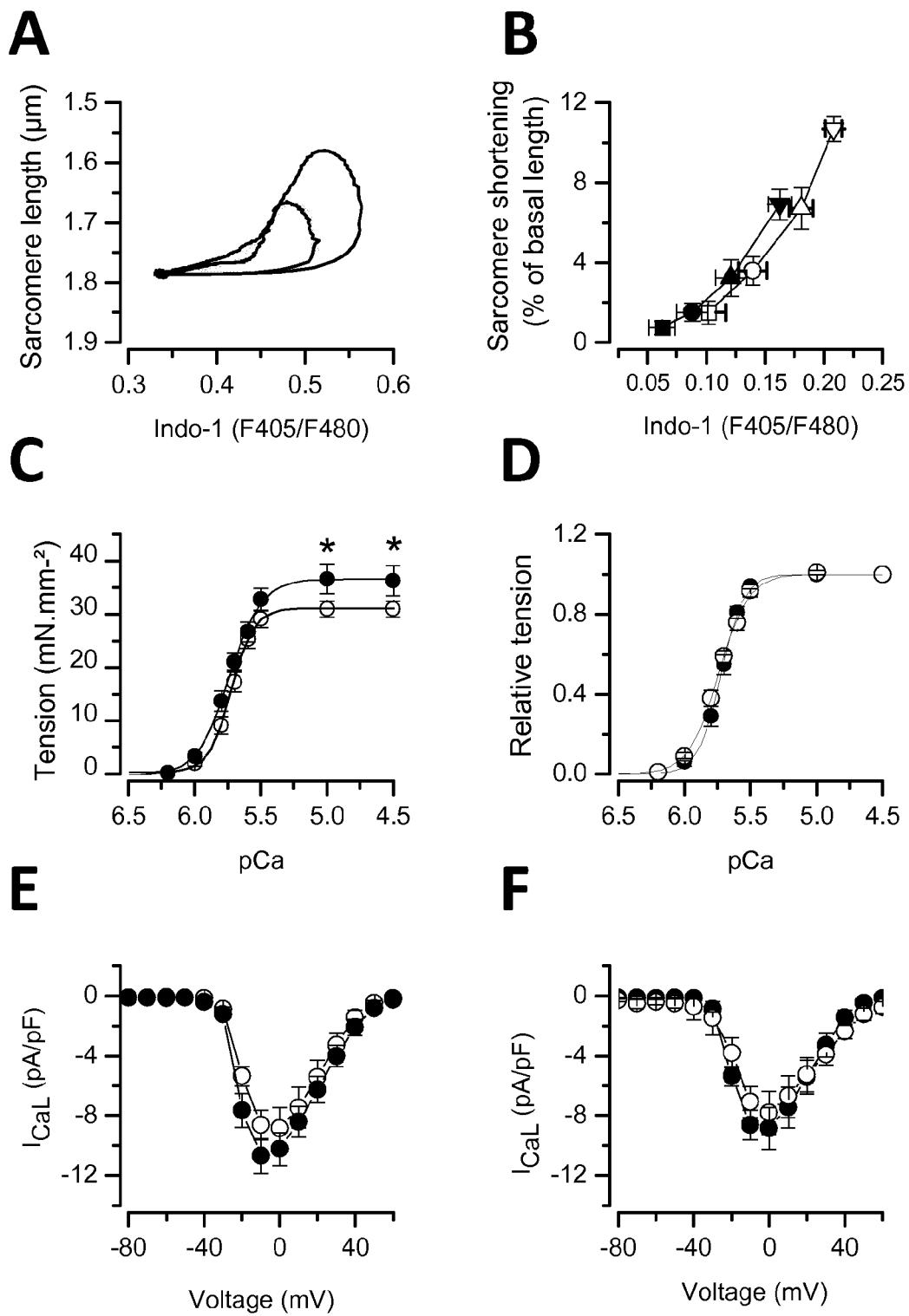

FIG. 3 Shh signal pathway on the cardiac excitation-contraction coupling. A) Representative traces of the relationships between $[Ca^{2+}]_i$ and shortening before and after a field stimulation in control (black line) ventricular cardiomyocytes and recombinant Shh (N-Shh)-treated (dash line) and Shh-harboring MPs ($MPs^{Shh+}$)-treated (grey line) cardiomyocytes for 4 h. B) Sarcomere shortening (% of resting length) vs. $Ca^{2+}$ transient in control and $MPs^{Shh+}$-treated cardiomyocytes after modulating the $Ca^{2+}$ transient by different external $[Ca^{2+}]$ (square: 0.3, circle: 0.5, up triangle: 1, down triangle: 1.8 mM). C) Tension and D) relative tension of isometric skinned control and $MPs^{Shh+}$-treated cardiomyocytes (n=12 in each condition). L-type $Ca^{2+}$ current density ($I_{CaL}$ in pA/pF) as a function of membrane potential recorded in voltage-clamp in control (n=7), recombinant Shh (N-Shh)-treated (N-Shh, n=8) (E) and Shh-harboring MPs (MPs$^{Shh+}$)-treated (n=8) (F) cardiomyocytes for 4 h. Data are mean±SEM, *, p<0.05 vs. control.

Figure 4:
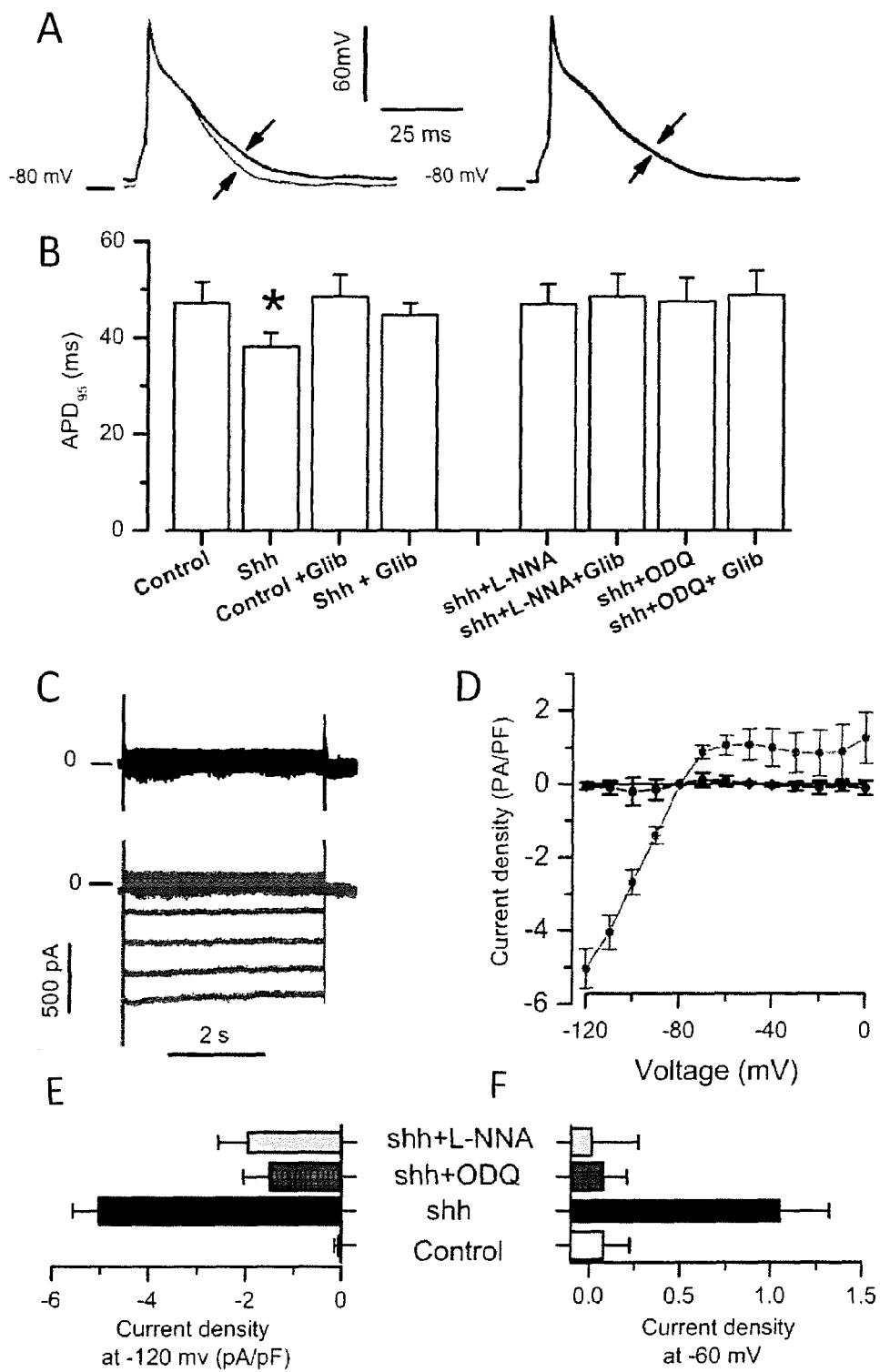

FIG. 4: Shh reduces action potential duration and activates an inward rectifying potassium current. A) Representative traces of action potential recorded in control and after Shh treatment (left panel, black and red grey). The same experiments were repeated in the presence the IKATP inhibitor glibenclamide (1 µM) (black control, grey Shh, right panel). Average values of action potential duration at 95% of the repolarization ($APD_{95}$, B) in control (n=7), Shh (n=8), Control+glibenclamide (n=7), Shh+glibenclamide (n=8), Shh+L-NNA (n=7), Shh+L-NNA+glibenclamide (n=7), Shh+ODQ (n=7), Shh+ODQ+glibenclamide (n=7). C) Family of current difference measured before and after application of glibenclamide from −120 mV to 0 mV in the absence (black traces) or in the presence of Shh (grey traces). Average steady state currents expressed as current density are represented in (D) (n=8 and 8 in control and Shh). Similar experiments were also performed in the presence ODQ (n=6) and L-NNA (n=6). The average current density at −120 and −60 mV is represented in (E) and (F), respectively. Data are expressed as mean±SEM, * and #, p<0.05 vs. control and Shh, respectively.

Figure 5:
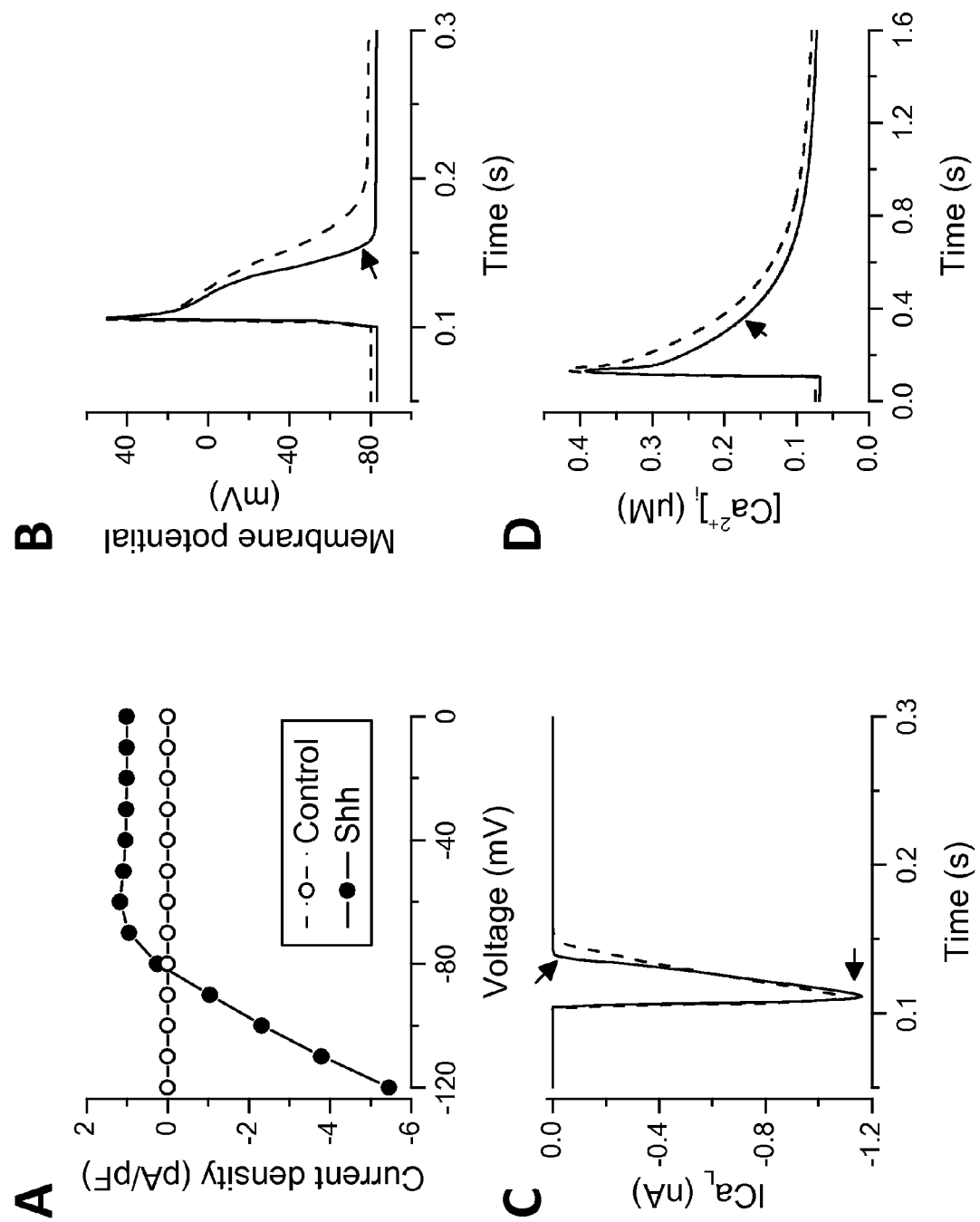

FIG. 5: Numerical simulation of action potential, $I_{CaL}$ and $Ca^{2+}$ transient with and without an additional inward-rectifying $K^+$ current. An equation matching for the inward rectifying current elicited by Shh was empirically built and added to the model (online model of Bondarenko et al. (2004) from the CellML). A) Current-voltage relationship of the current simulated. Time course of the action potential (AP) following an electrical stimulation (B) and time course $I_{CaL}$ during the AP (B) in the presence (black line) and in the absence (dash line) of this potassium current. It is to note that the shorter AP during Shh treatment elicited a higher but shorter $Ca^{2+}$ current, resulting in a lower net $Ca^{2+}$ influx (4.38 $E^{10}$ vs. 3.97 $E^{10}$ $Ca^{2-}$ ions in the absence and in the presence of the potassium current respectively) generating a smaller $Ca^{2+}$ transient (D).

Figure 6:
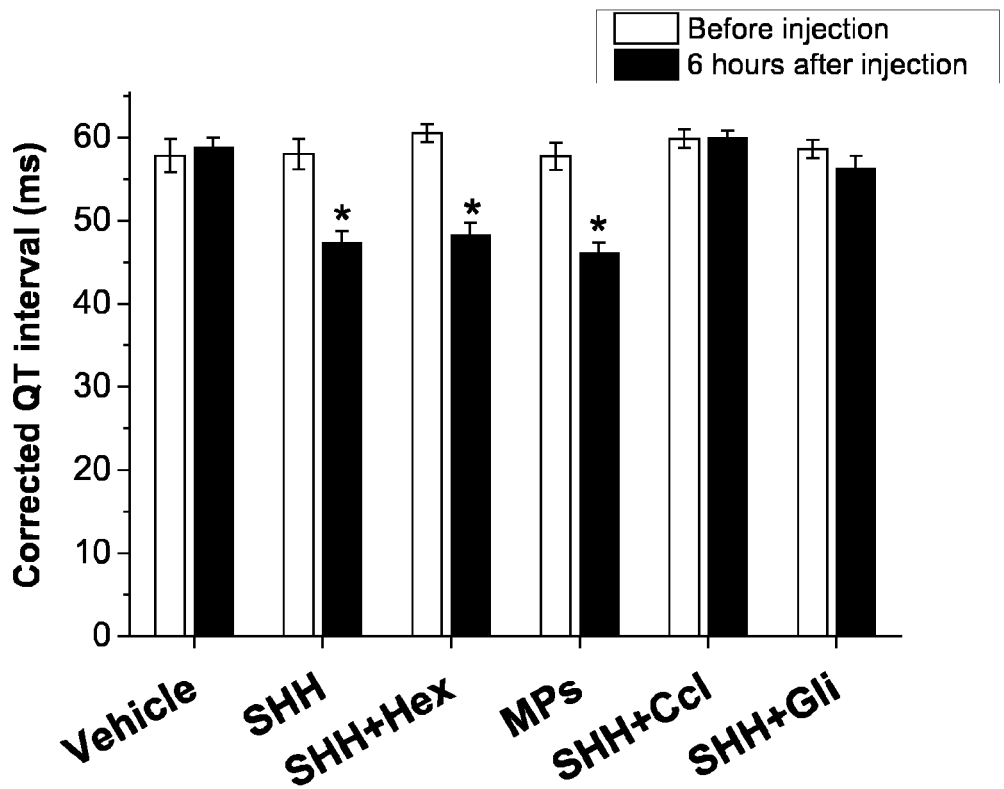

FIG. 6: Shh shortens QTc interval of ECG, 6 hours after IV injection. Telemetric ECGs were recorded in rats before and 6 hours after i.v. injection of Shh, Shh and hexamethonium, MPs, Shh and cyclopamine, Shh and glibenclamide. QT interval was corrected for the heart rate (see methods) and averaged over a period of 30 minutes. *p<0.05, 6 hours after IV injection vs. before injection FIG. 7: Time course of QTc interval after ischemia reperfusion. ECGs were recorded in rats before ischemia and during the first 24-hours of reperfusion. The coronary artery was occluded for 30 minute. Rats were i.v. injected 15 min before reperfusion Shh, Shh and cyclopamine or with the vehicle. QT interval was corrected for the heart rate (see methods) and averaged over a period of 30 minutes. (*P<0.05 vs. control).

Figure 8:
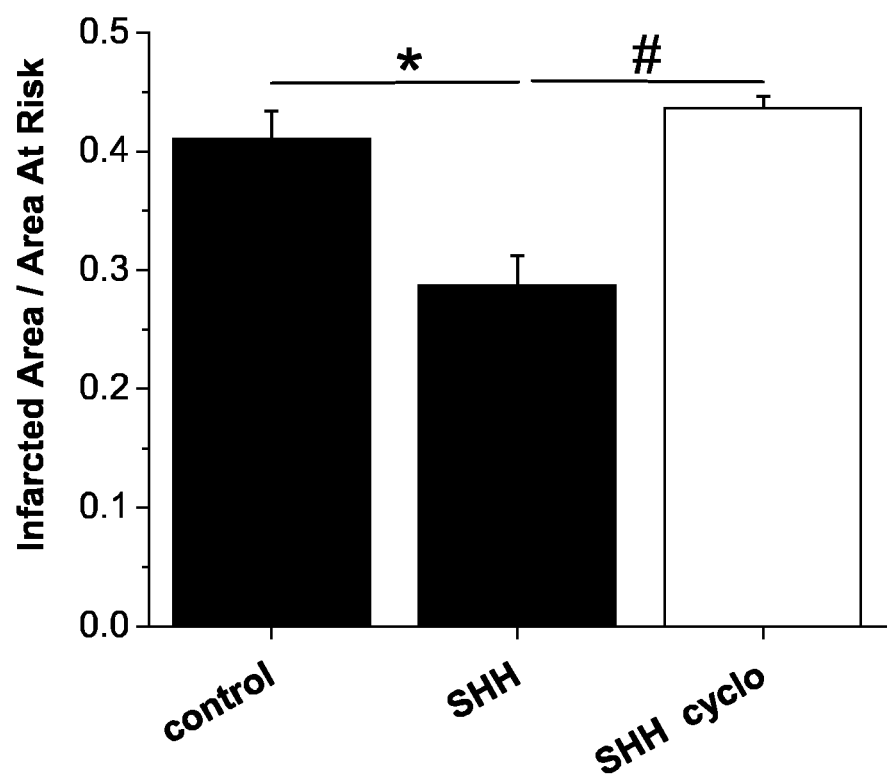

FIG. 8: Left ventricular remodeling 24 h after reperfusion. Heart sections stained with Masson trichrome revealed a major increase in fibrosis that was prevented when animals were i.v. injected with Shh, 15 min prior to reperfusion. This prevention was abolished by cyclopamine (*P<0.05 Shh vs. vehicle, #P<0.05 Shh vs. Shh+cyclopamine).

Figure 9:
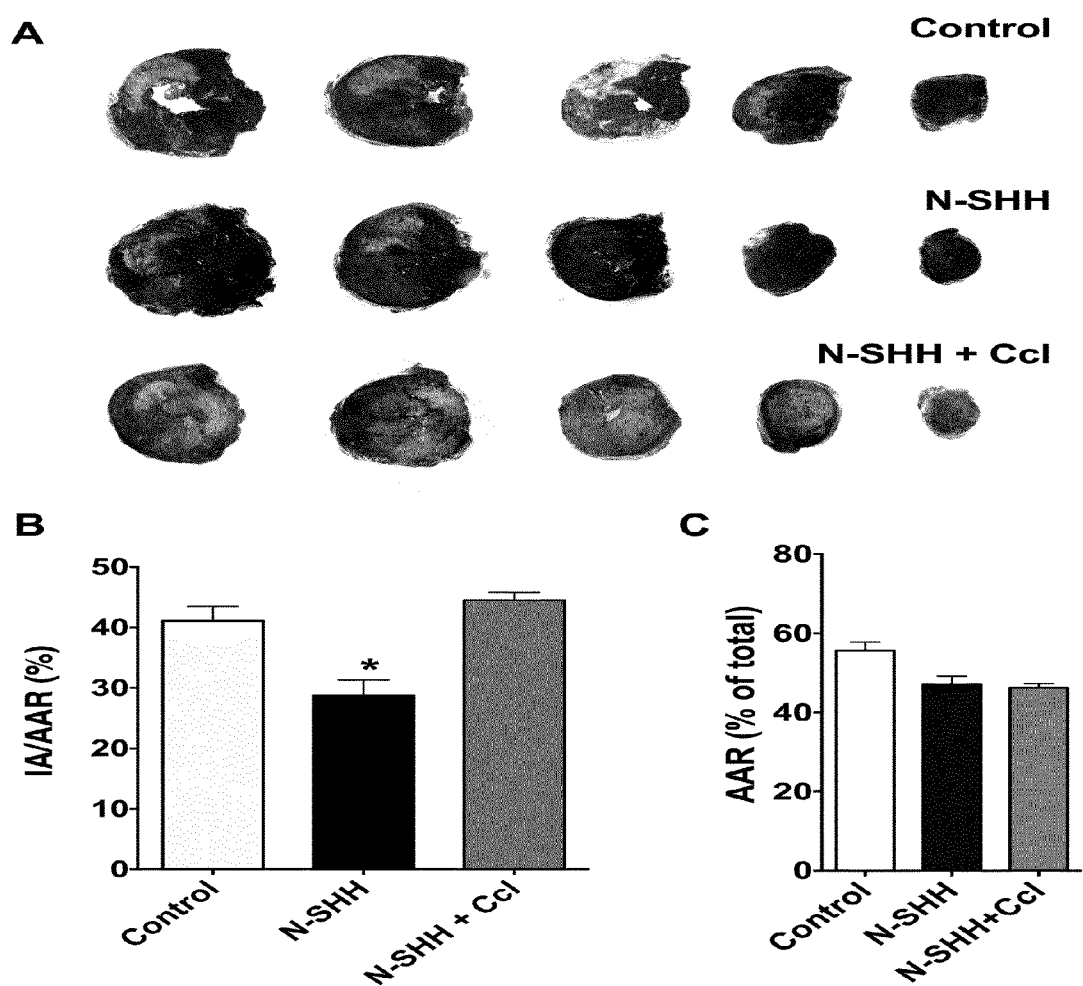
Figure 10A:
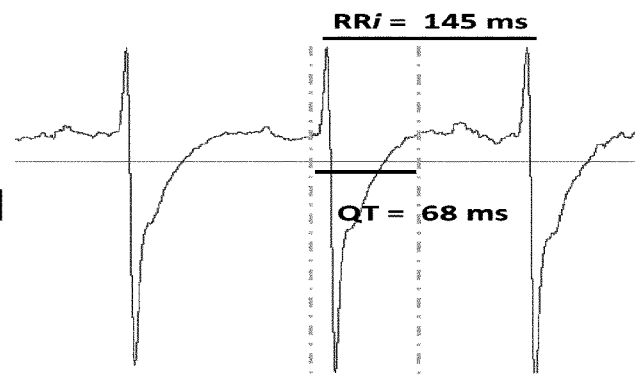
Figure 10A:
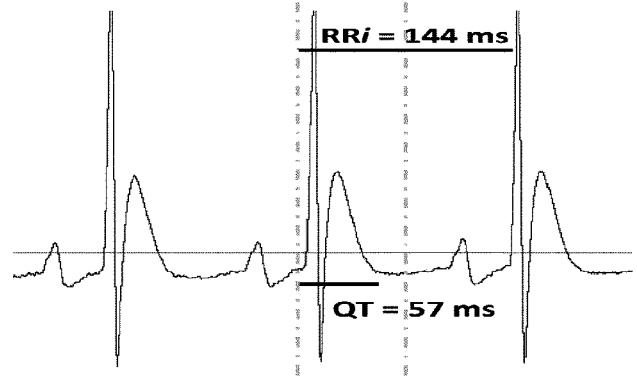
Figure 10A:
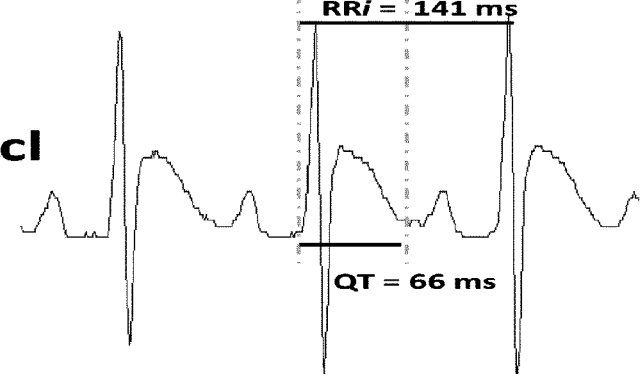
Figure 10B:
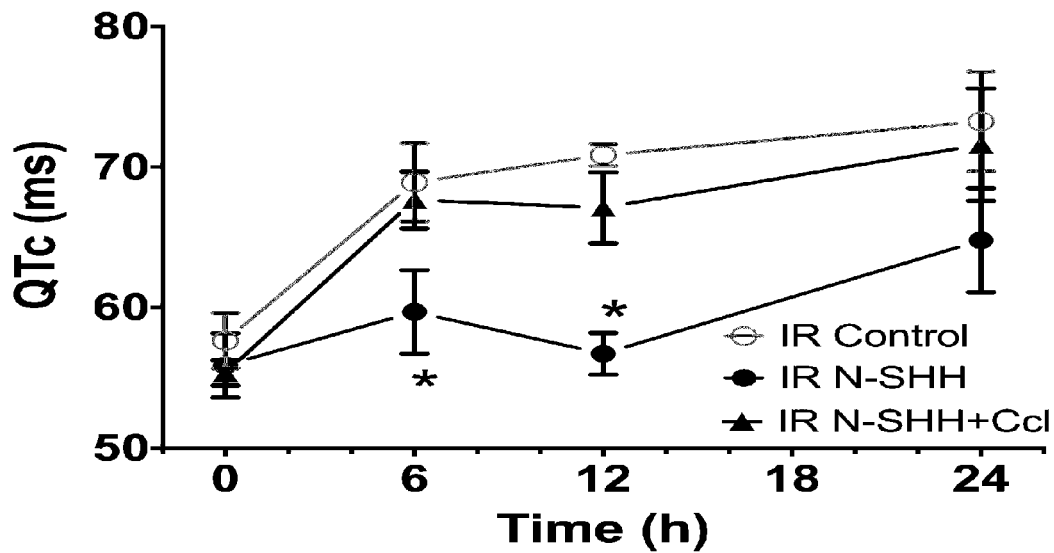
Figure 10C:
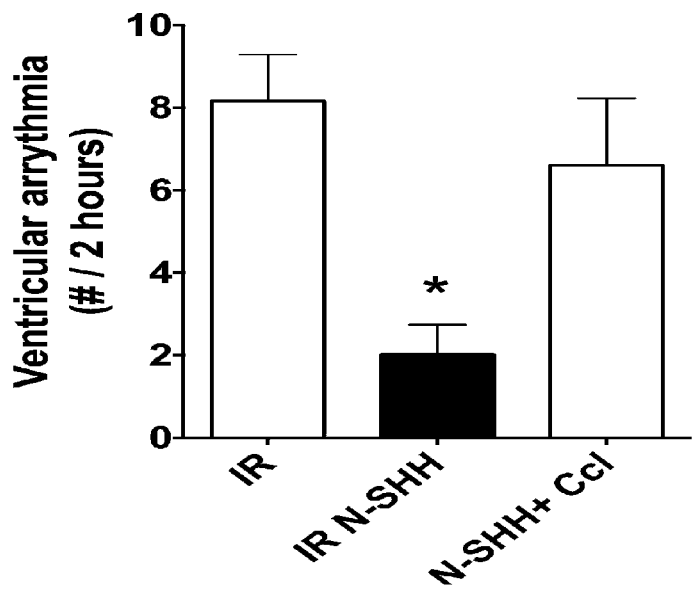
Figure 10D:
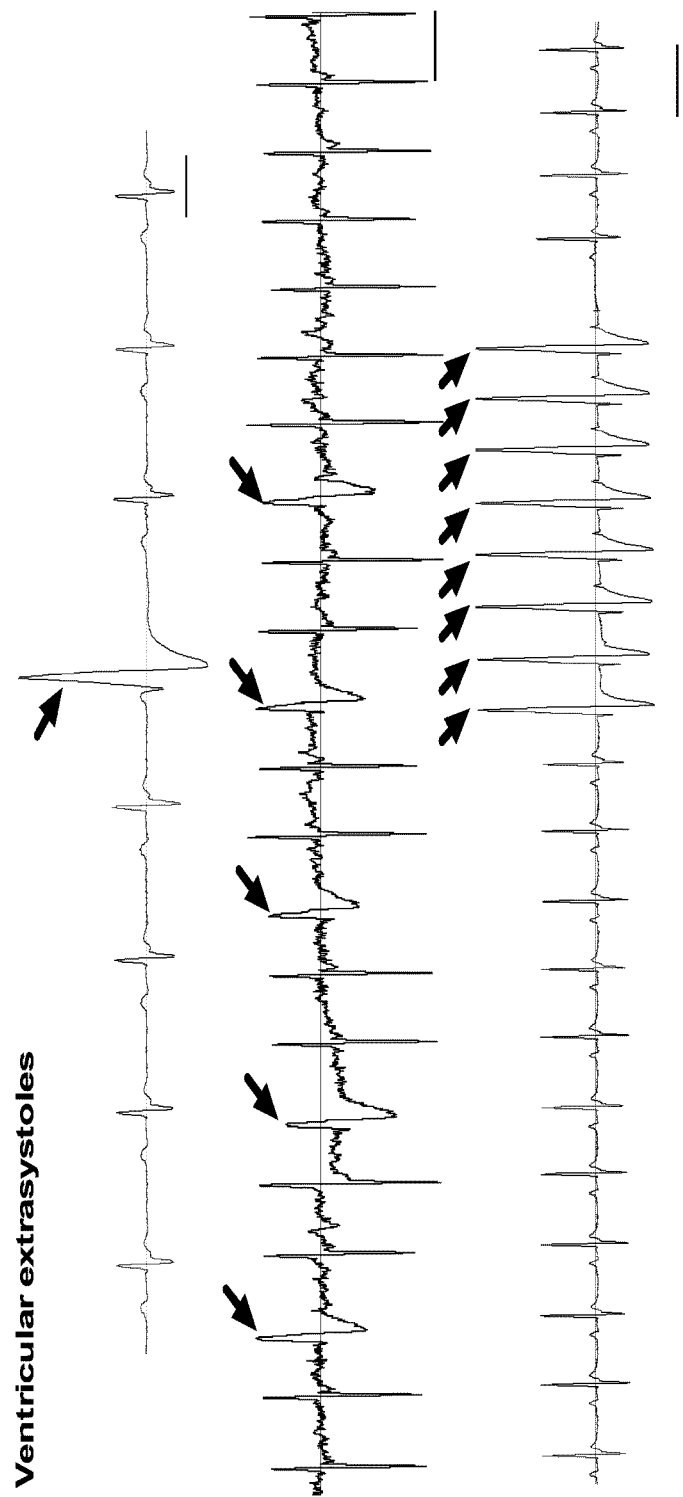

FIG. 9: Activation of the Shh pathway decreases the infarct size in a rat model of ischemia reperfusion. A) Representative sections (Upper) of TTC-stained hearts. B) Quantification was done by normalizing the infarct area (IA) to the area at risk (AAR). Treatment with N-Shh reduced infarct size after 24 h of reperfusion and this cardioprotective effect was prevented by cyclopamine. No significant difference was observed in the total AAR between groups (C). Data are expressed as mean±SEM (control n=6, N-Shh n=5, N-Shh+Ccl n=6; *p<0.05 vs control).

FIG. 10: Activation of Shh signaling improves ventricular repolarization after ischemia-reperfusion. ECGs were acquired over 24 h of reperfusion following 30 min ischemia, in animal treated (i.p. injected 15 min prior reperfusion) either with the vehicle, recombinant N-Shh, or N-Shh+Cyclopamine (Ccl). (A) Typical ECGs at 6 hours post reperfusion exhibited an enlargement of QT interval corrected for heart rate (QTc). Time course of QTc variation is summarized in (B) in the 3 different experimental conditions. C) Summarizes the number of arrhythmias recorded over a period of 2 hours following reperfusion showing a reduction of ventricular arrhythmia when SHH signaling pathway is activated. D) Three representative patterns of ventricular arrhythmias (indicated by arrows) recorded after reperfusion in animals treated with the vehicle only (control). (control n=6, N-SHH n=5, N-SHH+Ccl n=6; *p<0.05).

EXAMPLE 1

Sonic Hedgehog Signaling Modulates Excitation-Contraction Coupling in Adult Ventricular Myocytes Material & Methods Ethics Statement The experiments conformed to the National Institutes of Health Guide for the Care and Use of Laboratory Animals (NIH Pub. No. 85-23, Revised 1996) and All procedures conformed to the European Parliament Directive 2010/63/EU and the Council of 22 September 2010 on the protection of animals".

Isolated Cell Preparation

Ventricular cardiomyocytes were isolated from 200-250 g male adult Wistar rats as previously described[1]. The rats were anesthetized by i.p. injection of pentobarbital sodium (100 mg/kg) with heparin (100 U). The heart was rapidly excised, rinsed in ice-cold Hanks-HEPES buffer (in mM: NaCl 117, KCl 5.7, NaHCO$_3$ 4.4, KH$_2$PO$_4$ 1.5, MgCl$_2$ 1.7, HEPES 21, glucose 11.7, taurine 20, pH at 7.15) mounted on a Langendorff perfusion system and perfused (3 ml/min, at 37° C.) first with Hanks-HEPES buffer for 5 min to be cleared from blood and then with buffer supplemented with 1.2 mg/ml collagenase type 4 (Worthington, Lakewood, N.J., USA) for 13-18 min. The heart was placed into Hanks-HEPES buffer supplemented with 1 mg/ml 2,3-Butanedione monoxime (BDM) and 1 mg/ml BSA. The atria were removed and the ventricles were gently dissociated with scissors and pipettes in the same medium. The suspension was filtered through a nylon mesh (200 µm) and 4× incubated for decantation of the cells for 10 min. After each decantation of the supernatant, myocytes were resuspended in a Hanks-HEPES buffer containing 0 mmol/L $Ca^{2+}$ (+1 mg/ml BDM and 1 mg/ml BSA), 2 times in Hanks-HEPES buffer containing 0.3 mmol/L $Ca^{2+}$ (+0.6 mg/ml BDM and 1 mg/ml BSA) and finally Hanks-HEPES buffer containing 1 mmol/L $Ca^{2+}$ (+1 mg/ml BSA only).

Incubation with Shh Protein or Microparticles

Cells were counted and seeded to 150.10$^3$ cells/ml and subsequently incubated with 0.4 µg/ml recombinant human carrier bound Shh (C24II) protein (N-Shh, R&D Systems, Minneapolis, Minn., USA) or 10 µg/ml microparticles (MPs) for 4 hours at 22° C. while being gently shaken. The time for incubation was determined according to preliminary experiments in which incubation for 0 h, 2 h, 4 h and 6 h was tested and the effects on calcium transient and shortening were most pronounced after 4 h.

Microparticle Preparation

Microparticles (MPs) were obtained from the human lymphoid CEM T cell line (ATCC, Manassas, Va., USA). Cells were seeded at $10^6$ cells/ml, cultured in serum-free X-VIVO 15 medium (Lonza, Walkersville, Md., USA) and then treated subsequently with phytohaemagglutinin (5 μg/ml) for 72 h, with phorbol-12-myristate-13 (20 ng/ml) and actinomycin D (0.5 μg/ml) for 24 h ($MPs^{Shh+}$) or only with actinomycin D (0.5 μg/ml) for 24 h ($MPs^{Shh-}$). A supernatant was obtained in two centrifugation steps at 750 g for 15 min and at 1500 g for 5 min to remove cells and large debris. Remaining MP-containing supernatant was subjected at 14,000 g for 45 min to pellet MPs. MP pellet was subjected at two series of centrifugations at 14,000 g for 45 min. Finally, MP pellet was recovered in 400 μl sterile NaCl (0.9% w/v)[2]. MP content was adjusted to protein content determined against bovine serum albumin (BSA) standards to contain 10 μg proteins per ml.

Inhibitors and Chemicals

Control cells and cells loaded with MPs were also incubated under the same conditions as described above with different inhibitors: cyclopamine (Ccl, 30 μM, Shh pathway inhibitor), LY294002 (LY, 25 μM, PI3-K inhibitor), $N^{\omega}$-nitro-L-arginine (L-NNA, 100 μM, NOS inhibitor, 1H-[1.2.4]oxadiazolo[4.3-a]quinoxalin-1-one (ODQ, 10 μM, soluble guanylate cyclase, sGC, inhibitor), glibenclamide (Glib, 1 μM, $K_{ATP}$ channel inhibitor). Unless stated, all chemicals were obtained from Sigma (St. Louis, Mo., USA).

$Ca^{2+}$ Transient and Cell Shortening

Isolated ventricular cardiomyocytes were loaded with Indo-1 AM (10 μM, Invitrogen, Molecular Probes, Eugene, Oreg., USA) at room temperature for 30 min and then washed out with free HEPES-buffered solution (117 mmol/L NaCl, 5.7 mmol/L KCl, 4.4 mmol/L $NaHCO_3$, 1.5 mmol/L $KH_2PO_4$, 1.7 mmol/L $MgCl_2$, 21 mmol/L HEPES, 11 mmol/L glucose, 20 mmol/L taurine, pH 7.2) containing 1.8 mmol/L $Ca^{2+}$. Unloaded cell shortening and calcium concentration $[Ca^{2+}]$ (Indo-1 dye) were studied using field stimulation (1 Hz, 22° C., 1.8 mmol/L external $Ca^{2+}$). Sarcomere length (SL) and fluorescence (405 and 480 nm) were simultaneously recorded (IonOptix Myocyte Calcium and Contractility Recording System, Dublin, Ireland)[3]. To assess the calcium transient and shortening at different $[Ca^{2+}]_{out}$ (in mmol/L: 0.3, 0.5, 1, 1.8, 2.5, 3.5, 5), cardiomyocytes were placed on coverslips precoated with laminin and perfused at constants flow of 500 μ/min. Perfusion was achieved by placing a conical tip in the vicinity of the cell that was coupled to micro capillaries connected to 5 ml syringes.

Mechanical Recording and SL Measurement

The $Ca^{2+}$-activated force of single permeabilized myocytes was measured as described previously[3]. Intact isolated ventricular myocytes were permeabilized in a relaxing solution (pCa 9; pCa=−log $[Ca^{2+}]$, see below) containing 0.3% vol/vol Triton X-100 and protease inhibitors (phenylmethylsulfonyl fluoride (PMSF), leupeptin, and trans-epoxysuccinyl-1-leucine-guanidobutylamide (E-64)) at room temperature for 6 min. Cells were then rinsed twice with the same solution without Triton X-100 and maintained at 4° C.

Permeabilized myocytes were attached to a piezoresistive strain gauge (AE801 sensor, Memscap; 500 Hz unloaded resonant frequency, compliance of the strain gauge: 0.03 μm/μN) and to a stepper motor-driven micromanipulator (MP-285, Sutter Instrument Company) with thin stainless steel needles and optical glue (NOA 63, Norland Products) that is polymerized by 2 min UV illumination. SL was determined online during the experiment by applying a fast Fourier transform algorithm on the video images of the cell, using IonOptix acquisition software. Force was normalized to the cross-sectional area measured from the imaged cross-section. Slack SL was measured before attachment to serve as the origin. pCa-force relationships were established at 2.3 μm SL at 22° C. The active tension at each pCa was represented by the difference between total tension and relaxed tension. Cells that did not maintain 80% of the first maximal tension or a visible striation pattern were discarded. Although cells were kept isometric during contraction, sarcomeres typically changed length, especially when activation was maximal. Only cells that were well attached and with a minimal SL change (<0.1 μm) were kept. Active tensions at submaximal activations were normalized to maximal isometric tension (obtained at pCa 5). Force measurements were low-pass filtered at 100 Hz and recorded on a thermal paper recorder (Dash IV, Astro-Med). A single cell was positioned at the tip of a conical micro capillary that received the outlet of 10 micro capillaries connected to 5-mL syringes containing experimental solutions with a range of $Ca^{2+}$ concentration from pCa 9 to pCa 4.5 (flow rate 200 μl. $min^{-1}$). For each cell, the relation between force and pCa was fitted to the equation force=$[Ca^{2+}]^{nH}/(K+[Ca^{2+}]^{nH})$ where nH is the Hill coefficient and pCa50 is the pCa for half-maximal activation, corresponding to −(log K)/nH.

$Ca^{2+}$ activating solutions were prepared daily by mixing relaxing (pCa 9.0) and maximal activating (pCa 4.5) stock solutions. The relaxing and activating solutions contained 12 mmol/L phosphocreatine, 30 mmol/L imidazole, 1 mmol/L free $Mg^{2+}$, 10 mmol/L EGTA, 3.3 mmol/L $Na_2ATP$, and 0.3 mmol/L DTT with either pCa 9.0 (relaxing solution) or pCa 4.5 (maximal activating solution), pH 7.1 adjusted with KOH. Ionic strength was adjusted to 180 mmol/L with K-acetate.

Nitric Oxide (NO) Measurement

Cardiomyocytes were loaded with the NO sensitive fluorescent dye: DAF-AM (20 μM, 4-amino-5-methylamino-2,7-difluorofluorescein diacetate, for 30 min, Invitrogen). Cells were then resuspended in Tyrode's solution (1.8 mmol/L $Ca^{2+}$) at 22° C. DAF fluorescence confocal images were acquired in the x-y mode (Zeiss LSM 510, 25×, NA=0.8 water immersion, Le Pecq, France), with 488 nm excitation with argon ion laser and 510-530 nm emission filter. The fluorescence values were corrected for the background fluorescence from a region of the image without cells $(F-F_0)$ and fluorescence/background ratio $((F-F_0)/F_0)$ was calculated. All images were processed and analyzed using Image J v 1.36b software (National Institute of Health, USA).

Western Blot

Proteins were extracted from cardiomyocytes-pellets homogenized in lysis buffer (10 mmol/L Tris-malate, 20 mmol/L β-glycerolphosphate, 50 mmol/L NaF, 10 mmol/L benzamidine, 0.2 mmol/L $Na_3VO_4$, 40 μM leupeptin, 500 μM PMSF, 10 μM E64, 2 mmol/L EDTA, 5 mmol/L DTT, 1% Triton X100, pH 6.8, at 4° C.). The homogenates were centrifuged at 10,000 g for 5 min at 4° C. Total protein concentration was determined by RC DC kit (Bio-Rad, Hercules, Calif., USA). The protein extracts were solubilized in Laemmli-urea buffer (10 mmol/L Tris-malate, 20 mmol/L β-glycerolphosphate, 50 mmol/L NaF, 10 mmol/L benzamidine, 0.2 mmol/L $Na_3VO_4$, 40 μM leupeptin, 500

μM PMSF, 10 μM E64, 1 mmol/L EDTA, 1 mmol/L EGTA, 8 M urea, 2 M thio-urea, 3% SDS, 5 mmol/L DTT, 1% Triton X100, pH 6.8, at 4° C.) and boiled for 5 min at 95° C. Protein samples (50 μg) were separated using SDS-PAGE (10%) electrophoresis and transferred to polyvinylidene fluoride membrane by semi-dry western blot protocol and blocked with 3% BSA for 1 h at room temperature. Membranes were stained with goat antibody against Smo (ab58591) (1:400, Abcam, Cambridge Science Park, Cambridge, UK) and Ptc (sc-6147) (1:1,000, Santa Cruz Biotechnology, Inc, Santa Cruz, Calif., USA) overnight at 4° C. and peroxidase-conjugated secondary anti-rabbit (1:3,000)/anti-goat (1:1,0000) IgG antibodies (Pierce, Rockford, Ill., USA). The bands were identified using chemoluminescence (Super Signal West Pico, Pierce), densitometrically evaluated and expressed in arbitrary units (A.U.).

RNA Extraction and Real-Time RT-PCR

RNA was extracted from cardiomyocytes pellets using TRIzol reagent according to manufacturer's protocol (Euromedex, Souffelweyersheim, France), treated with DNase I (Invitrogen) at 37° C. for 30 min. cDNA was synthesized using superscript II reverse transcriptase (Invitrogen) at 42° C. for 50 min. Quantitative PCR was performed using a LightCycler rapid thermal cycler (Roche, Meylan, France). Twenty μl reaction mixture contained 10 μl of Absolute QPCR SYBR Green Capillary mix (thermo strat DNA polymerase, reaction buffer, deoxyrybonucleoside triphosphate mix, 3 mmol/LMgCl$_2$, SYBR green I dye; Thermo Fischer Scientific, llkirch, France) supplemented with 0.5 μM primer mix and 5 μl of cDNA. The data were normalized to GAPDH. The amplification program included the initial denaturation step at 95° C. for 15 min, 40 cycles of denaturation at 95° C. for 1 sec, annealing at 60° C. for 10 sec and extension at 72° C. for 20 sec. Melting curves were used to determine the specificity of PCR products.

Cellular Electrophysiology

Whole-cell patch-clamp experiments were performed at room temperature (22-24° C.) with an Axopatch 200B (Axon instrument, Burlingham, Calif., USA). Patch pipettes had resistance of 2 MΩ. Currents were normalized to the cell membrane capacitance (pA/pF). Series resistances were compensated before recordings.

To record APs, pipettes solution contained (in mM): KCl (130), HEPES (25), ATP(Mg) (3), GTP(Na) (0.4), EGTA (0.5); pH 7.2 (KOH). Bathing solution contained (in mmol/L): NaCl (135), MgCl (1), KCl (4), Glucose (11), HEPES (2), CaCl (1.8); pH 7.4 (NaOH). APs were elicited by 0.2 ms current injection of supra-threshold intensity. During experiments, cells were stimulated by trains of 30 stimuli at 0.5 Hz.

To record $I_{CaL}$, bath solution contained (in mM): CaCl$_2$ (1.8), TEACl (140), MgCl$_2$ (2), glucose (10), HEPES (10), pH 7.4 (TEAOH). Pipette solution contained (in mmol/L): CsCl (140), HEPES (10), EGTA (10), NaGTP (0.4), MgATP (3), pH 7.2 (CsOH). $I_{CaL}$ was elicited by test depolarization (150 ms) from −80 to −10 mV at 0.1 Hz. Current-voltage relationship was determined using 10 mV voltage step from −80 to +50 mV. Its amplitude was estimated as the difference between peak $I_{CaL}$ and current level at the end of the pulse.

K$^+$ currents were recorded with the solution used for APs, but with 10 μmol/L tetrodotoxin (TTX) and 2 mM cobalt (Co$^{2+}$) added in the external medium to block $I_{Na}$ and $I_{CaL}$, respectively. They were elicited from a holding potential (HP) of −80 mV by test depolarization (1s) ranging from −120 mV and 0 mV at 0.1 Hz. Voltage steps were performed 2 times on each cells before and after glibenclamide application and used to determine the glibenclamide sensitive components of the current.

Numerical Simulation

The numerical simulation was performed using the mouse endocardial ventricular cell model described by [4]. This model is available online from the CellML repository (see the website located at cellML.org) and was developed with Cellular Open Resource[5]. The current activated by Shh was simulated by the following equation derived from an instantaneous inward rectifying current equation having a negative slope:

$$i_{shh} = \frac{g_{shh} \cdot (V - E_K)}{1 + e^{\frac{F \cdot (V - E_K)}{R \cdot T}}} + \left(1 - \frac{1}{1 + e^{\frac{F \cdot (V - E_K)}{R \cdot T}}}\right) \cdot 0.1$$

where $E_K$ is the equilibrium potential for K$^+$, $G_{shh}$, is the $I_{shh}$ conductance, R is the gas constant, T is the temperature and F the Faraday constant.

Histology.

Thin sections (5 μm) were prepared from the rat left ventricles and stained with Haematoxylin-Eosin (HE) and Masson trichrome (MT) for light microscopy (10×). The thickening of the myocardium was estimated on the HE-stained heart sections, and the presence of collagen was analyzed on the MT-stained ventricle sections. Results indicate the percent of fibrosis area expressed as a percentage of collagen content area of myocardial tissue analyzed.

Recording and Analysis of ECG.

Rats were implanted with DSI PhysioTel™ Transmitter (CTA-F40, Data Sciences International, Saint-Paul, Minn., USA), fifteen days before starting experiments. After recovery, ECGs were recorded by using a signal transmitter-receiver (RPC-1; DSI) connected to a data acquisition system (IOX2; EMKA Technologies). The data were collected continuously at a sampling rate of 1,000 Hz. Thus, ECGs were recorded in rats before and 6 hours after i.v. injection of Shh, Shh and hexamethonium, MPs, Shh and cyclopamine, Shh and glibenclamide. ECGs were also monitored 24 h before ischemia, during ischemia and 24 h after reperfusion. Continuous digital recordings were analyzed offline by using the software ECG-auto (ver 1.5.12.22, EMKA Technologies). ECG signals were digitally filtered between 0.1 and 1,000 Hz. The heart rate and QT interval were measured. The QT interval was defined as the time between the first deviation from an isoelectric PR interval until the return of the ventricular repolarisation to the isoelectric TP baseline from lead II ECGs. The QT interval is dependent on the heart rate, therefore, QT interval should be corrected to take into account potential changes in RR interval. The QT correction was performed according to the Bazett's formula:

$$QTB = \frac{QT}{\sqrt{RR}}$$

where $QT_B$ is the QT interval corrected for heart rate, and RR is the interval from the onset of one QRS complex to the onset of the next QRS complex.

Statistics

Presented numerical data are Mean±standard error of mean (SEM). Results were considered significant if p<0.05, with one-way, two-tailed Analysis of Variance (ANOVA) with Bonferroni post-test.

Results

Shh Pathway is Functional in Adult Cardiomyocytes

Two transmembrane proteins Patched (Ptc) and Smoothened (Smo) have been identified as the hedgehog receptor complex[24, 25]. Ptc functions as hedgehog-binding protein while Smo is required to transduce the signal. In the absence of hedgehog signal, Ptc inhibits the activity of Smo, when hedgehog interacts with Ptc, Ptc is internalized and Smo inhibition is removed[25]. PCR analysis leads to the identification of the presence of mRNA encoding Ptc and Smo in isolated adult rat ventricular myocytes (FIG. 1A). This was further confirmed by Western blot revealing the presence of Ptc and Smo (FIG. 1B). Cardiomyocytes were then loaded with the NO fluorescent probe, DAF (FIG. 1C). In a first series of experiments, cells were incubated with the recombinant protein of Shh homolog ligand (N-Shh) for 4 hours at 20 μmol/L. When compared to control cells, DAF fluorescence was significantly increased after N-Shh incubation suggesting a production of NO. This effect was prevented in the presence of the NOS inhibitor L-NNA. PI3K is known as a potential upstream NOS modulator[16]. Shh-induced NO production was also inhibited in the presence of PI3K inhibitor LY29402. NO production was also significantly increased when cardiomyocytes were incubated for 4 hours with shed membrane MPs harboring the Shh ligand (MPs$^{Shh+}$,[18]). This effect was prevented when cardiomyocytes were pre-incubated with the specific inhibitor of the Shh pathway, cyclopamine. When cells were incubated with different MPs lacking the Shh ligand (MPs$^{Shh-}$,[18]), DAF fluorescence was comparable to control. All together, these experiments demonstrate that Shh pathway is present and functional in adult rat cardiomyocytes, and linked to NOS activation and NO production most likely through the PI3K/Akt upstream pathway.

Shh Pathway Modulates Excitation-Contraction Coupling

Isolated cardiomyocytes were loaded with indo-1 (5 μM for 20 min) and paced at 0.5 Hz. Sarcomere length variations and cytosolic $Ca^{2+}$ were simultaneously recorded. The cell shortening triggered by the electrical stimulation was reduced by both N-Shh and MPs$^{Shh+}$ treatments (FIG. 2A, E) without affecting the resting sarcomere length (FIG. 2B). N-Shh or MPs$^{Shh+}$ also reduced significantly $Ca^{2+}$ transient amplitude (FIG. 2C, F), while the diastolic $Ca^{2+}$ remained statistically unchanged although slightly decreased (FIG. 2D).

Experiments were conducted to evaluate the impact of Shh-induced NO production on cell shortening (FIG. 2E) and $Ca^{2-}$ transient (FIG. 2F) in cardiomyocytes. The reduction of cell shortening and $Ca^{2+}$ transient amplitude induced by N-Shh was fully abolished in the presence of Shh pathway inhibitor cyclopamine, PI3K inhibitor LY249002 and the non-selective NOS inhibitor, L-NNA. The effect of N-Shh mimicked by the shed membrane MPs$^{Shh+}$ was also blocked by cyclopamine while MPs$^{Shh-}$ had no effect.

This reduction in cell shortening might be in part the consequence of either the reduced $Ca^{2+}$ transient amplitude and/or eventually direct action at the level of the contractile machinery. The relationships between $Ca^{2+}$ transient and sarcomere length cell shortening was first represented as phase-plane loops (FIG. 3A,[26]). This type of representation reflects the kinetic response of the contractile machinery to changes in $Ca^{2+}$. This shows a first phase of rapid $Ca^{2+}$ rise with little contractile response followed by a cell shortening that begins at the peak of $Ca^{2+}$ transient. The contractile response continues even as $Ca^{2+}$ falls and finally, both $Ca^{2+}$ and contraction decline together. Thus, the reduction in cell shortening is correlated with the reduced $Ca^{2+}$ transient after Shh stimulation. To modulate $Ca^{2+}$ transient amplitude and myofilament response, cells were bathed in various $[Ca^{2+}]_{out}$ ranging from 0.3 to 5 mmol/L (FIG. 3B). For each outside $[Ca^{2+}]$, sarcomere shortening was plotted against peak $Ca^{2+}$ transient amplitude. The curves obtained from control and MPs$^{Shh-}$ treated cardiomyocytes were superimposed, however with a shift toward lower $Ca^{2+}$ transients and shortening in MPs$^{Shh+}$. Finally, myofilament $Ca^{2+}$ sensitization was evaluated in Triton-X100 skinned cardiomyocytes[21]. As shown in FIG. 3C-D, the tension-pCa relationships demonstrated a similar $Ca^{2+}$ sensitization of the myofilament ($pCa_{50}$=5.91±0.03 and 5.87±0.03 in control and MPs$^{Shh+}$ conditions, respectively, n=12 cells per condition). A slight increase in maximal active tension was observed under MPs$^{Shh+}$ treatment for pCa above 5.5. All together, these support the hypothesis that the reduction in cell shortening by N-Shh and MPs$^{Shh+}$ is the consequence of a reduced $Ca^{2+}$ signaling.

We then evaluated the effect of N-Shh and MPs$^{Shh+}$ on the main cardiac $Ca^{2+}$ release trigger, i.e. the L-type $Ca^{2+}$ current ($I_{CaL}$, FIG. 3E,F) known to be modulated by $NO^{27}$. The activation of Shh pathway did not affect $I_{CaL}$ measured in voltage clamp conditions. Finally, sarcoplasmic reticulum (SR) $Ca^{2+}$ release measured as the peak $Ca^{2+}$ transient measured after a rapid application of 10 mmol/L caffeine was similar in control cells and cells incubated with either N-Shh or MPs$^{Shh+}$, (F405/F480 ratio=0.38±0.02 (n=63), 0.37±0.02 (n=24) and 0.36±0.02 (n=36) respectively) suggesting that Shh pathway might not interfere directly with the SR compartment.

Effect of Shh Pathway on the Action Potential $Ca^{2+}$ transient amplitude and cell contraction are directly modulated by the action potential waveform as a result of changes in $I_{CaL}$[28]. Cardiomyocytes pre-incubated with N-Shh exhibited a shorter action potential duration (APD) compared to control cardiomyocytes (FIG. 4AB). The NO/cGMP pathway has been recently described to activate neuronal ATP-dependent potassium channel (K-ATP) in the absence of ATP depletion[29-31]. Interestingly, acute application of glibenclamide, the selective and specific blocker of K-ATP channels,[32] prevented the APD reduction induced by N-Shh, although it had no effect in the absence of N-Shh treatment (FIG. 4B). Besides, blockade of NO/cGMP pathway by L-NNA and ODQ, respectively blunted the effect of N-Shh. Further electrophysiological experiments were performed to characterize the glibenclamide-sensitive $K^+$ current in voltage-clamp condition. $K^+$ currents were recorded prior to and after incubation with glibenclamide[32] and the current difference reflecting the K-ATP current ($I_{KATP}$, FIG. 4C) was measured at the end of the pulse to build the current voltage relationship (FIG. 4D). This current was absent in control condition (FIG. 4C-E), but elicited in the presence of N-Shh and was blocked by both L-NNA and ODQ. To corroborate these experiments, a numerical simulation was performed in the absence and the presence of an additional potassium inward rectifying current (see Methods section) empirically adjusted to best mimic the experimental results of the Shh-induced current recorded by subtraction before and after application of glibenclamide (FIG. 5A). Adding the inward rectifying $K^+$ conductance reduced the action potential duration (FIG. 5B) as well as the $Ca^{2+}$ transient (FIG. 5D) to the same extent as observed experimentally. This was accompanied by an increase in $I_{CaL}$ amplitude (FIG. 5C) but a reduction in the net amount of $Ca^{2+}$ entering the cell (4.38 $E^{10}$ vs. 3.97 $E^{10}$ $Ca^{2+}$ ions in control and Shh respectively) due to shorter $Ca^{2+}$ current and resulting in a reduced $Ca^{2+}$-induced $Ca^{2+}$ release as previously reported[28]. This demonstrate that the reduction in $Ca^{2+}$ transient elicited by the Shh pathway in the absence of a direct effect on the L-type $Ca^{2+}$ channels, results from the activation of $I_{KATP}$ and a subsequent reduction in APD.

Figure 7:
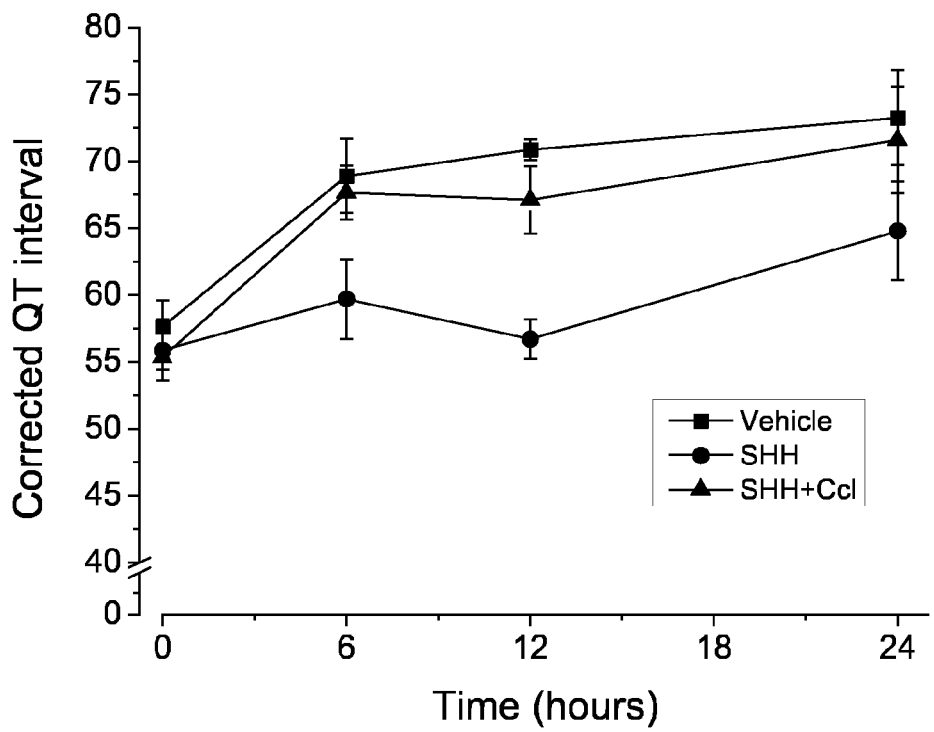

Such reduction in APD should impact the ECG recorded in vivo and more precisely the QT interval. As matter of fact ECGs were recorded during 6 h after injection of N-Shh and $MPs^{Shh+}$ ECGs in vigil unrestrained animal. A significant reduction in QTc interval was observed 6 h after injection (FIG. 6). This effect was identical when the animals were pre-treated with hexamethonium, a nicotinic nACh receptor antagonist that acts on receptors at pre-ganglionic sites in both the sympathetic and parasympathetic nervous systems and therefore inhibits cardiac regulation by autonomic nervous system. However this reduction in QTc interval was prevented both by blocking in vivo $I_{KATP}$ current with glibenclamide or by inhibiting Shh signaling pathway with cyclopamine (FIG. 6). QTc enlargement correlates in vivo with the occurrence of ventricular arrhythmias. This occurs in pathophysiological situations such as ischemia-reperfusion, which exhibits rapidly after myocardial reperfusion higher frequency of ventricular arrhythmias that may trigger sustained ventricular tachycardia and sudden death. To validate this hypothesis, we subjected rats to 30 min. ischemia followed by reperfusion. ECGs were continuously recorded before ischemia and during 24 h after reperfusion (FIG. 7). As reported previously, an enlargement of QTc interval was recorded after the reperfusion. Interestingly, this was fully abolished when the animals were treated with N-Shh prior to the reperfusion. It is to note that the maximal effect of N-Shh treatment was observed after 12 h of reperfusion. Knowing that a single injection of N-Shh is done prior to the reperfusion, one can expect that the progressive loss of effect observed after 24 h could be due to the loss of stimulation of Shh signaling pathway. No beneficial effect of N-Shh on the QTc interval could be seen when cyclopamine was injected in addition N-Shh (FIG. 7). Furthermore, the lesions of reperfusion were histologically evaluated at 24 h after reperfusion by measuring the infarcted area relative to the area at risk (FIG. 8). These experiments demonstrated a clear reduction in the infarcted area with N-Shh. This cardioprotective effect was fully abolished by cyclopamine. These in vivo data clearly demonstrate the potent role of Shh signaling pathway to protect the myocardium against the reperfusion injuries after an acute myocardial infarction.

EXAMPLE 2

Cardioprotective Effect of Shh Signaling Pathway

The rats were subjected to 30 min ischemia followed by reperfusion. The reperfusion injuries were histologically evaluated at 24 h after reperfusion by measuring the infarcted area relative to the area at risk (FIG. 9). Fifteen minutes prior to reperfusion, one group of rats received intravenous (iv) injection of the recombinant Shh homolog ligand (N-ShhH, 25 µg·$kg^{-1}$), the second group received N-Shh and the Shh receptor (patch/smoothened) antagonist cyclopamine (N-Shh+Ccl, 30 µmol/L) and the third one the vehicle (control). These experiments demonstrated a significant reduction of the infracted area with N-Shh treatment. This cardioprotective effect of N-Shh was fully prevented by cyclopamine. These in vivo data demonstrate the potent role of Shh signaling pathway to protect the myocardium against reperfusion injuries after acute myocardial infarction (AMI). Considering that the cardio-protective effects are observed within a short time after reperfusion (i.e. <24 h), it is unlikely that they are mediated by a neoangiogenesis and/or mobilization of progenitor cells (Kusano K F, Pola R, Murayama T, Curry C, Kawamoto A, Iwakura A, Shintani S, Ii M, Asai J, Tkebuchava T, Thorne T, Takenaka H, Aikawa R, Goukassian D, von Samson P, Hamada H, Yoon Y S, Silver M, Eaton E, Ma H, Heyd L, Kearney M, Munger W, Porter J A, Kishore R and Losordo D W. Sonic hedgehog myocardial gene therapy: tissue repair through transient reconstitution of embryonic signaling. Nat Med. 2005; 11:1197-204. Pola R, Ling L E, Silver M, Corbley M J, Kearney M, Blake Pepinsky R, Shapiro R, Taylor F R, Baker D P, Asahara T and Isner J M. The morphogen Sonic hedgehog is an indirect angiogenic agent upregulating two families of angiogenic growth factors. Nat Med. 2001; 7:706-11.). We therefore hypothesized for another pleiotropic effect of Shh directly on the myocardial tissue.

We evaluated the ECG continuously recorded before ischemia and during 24 h after reperfusion in vigil animal by telemetry (FIG. 10). After reperfusion, an enlargement of the QTc interval is observed. This is prevented in animal treated by a single injection of N-Shh prior to the reperfusion, without major undesired cardiodepressive effect on sinus rate. It is to note that the significance of this effect tends to disappear after 12 h probably due to the elimination of the peptide and reversion of its effect (FIG. 10A, 10B). When the animals were treated simultaneously with both N-Shh and cyclopamine (N-Shh+Ccl), the prevention of QTc enlargement was abolished (FIG. 10A, 10B). QT interval enlargement correlates in vivo with the occurrence of ventricular arrhythmias and is commonly used as a predictor for ventricular tachyarrhythmias and a risk factor for sudden cardiac death (Antzelevitch C, Shimizu W, Yan G X and Sicouri S. Cellular basis for QT dispersion. Journal of electrocardiology. 1998; 30 Suppl:168-75; Hlaing T, DiMino T, Kowey P R and Yan G X. ECG repolarization waves: their genesis and clinical implications. Annals of noninvasive electrocardiology: the official journal of the International Society for Holter and Noninvasive Electrocardiology, Inc. 2005; 10:211-23.). As a matter of fact, the treatment with N-Shh reduced significantly the number of ventricular arrhythmic events measured at the reperfusion (FIG. 10C-D). This beneficial effect of Shh is again abolished by cyclopamine. Altogether, these experiments demonstrate a direct cardioprotective effect of Shh pathway on the myocardium through an electrophysio logical regulation.

The present examples demonstrate first a novel cardioprotective effect of the morphogenetic Shh pathway in an in vivo model of ischemia-reperfusion in rats. Secondly we investigated the cellular and molecular levels and proposed a mechanistic explanation. It was previously reported that Shh signaling plays an important role in cardiomyogenesis during embryonic development. The restitution of this signaling in adult rats after myocardial infarction improved cardiac reparation by enhancing neovascularization, reducing fibrosis and cardiac apoptosis (Kusano K F, Pola R, Murayama T, Curry C, Kawamoto A, Iwakura A, Shintani S, Ii M, Asai J, Tkebuchava T, Thorne T, Takenaka H, Aikawa R, Goukassian D, von Samson P, Hamada H, Yoon Y S, Silver M, Eaton E, Ma H, Heyd L, Kearney M, Munger W, Porter J A, Kishore R and Losordo D W. Sonic hedgehog myocardial gene therapy: tissue repair through transient reconstitution of embryonic signaling. Nat Med. 2005; 11:1197-204.). It has been recently demonstrated that the stimulation of Shh at the surface membrane of cardiomyocytes was able to increase the expression of angiogenic cytokines mediating angiogenesis after myocardial infarction. The present Examples demonstrate that Shh pathway activation prior to reperfusion by a single injection of either N-Shh or MPs$^{Shh+}$, reduces infarct size and reperfusion arrhythmias via a prevention of QT enlargement. In several studies, prolongation of QT interval has been associated with an increased risk of sudden cardiac death after acute myocardial infarction in patients both in short and long term. It is now well admitted that reduction of QT interval and QT interval variability after reperfusion, is beneficial and indicative of a successful reperfusion in patients undergoing primary percutaneous coronary angioplasty. In conclusion, the present Examples show for the first time a direct protective effect of Shh pathway against AMI on cardiac tissue. All together these pleiotropic effects of Shh participates in cardioprotection by acting simultaneously on different targets.

REFERENCES

Throughout this application, various references describe the state of the art to which this invention pertains. The disclosures of these references are hereby incorporated by reference into the present disclosure.

1. Ericson J, Morton S, Kawakami A, Roelink H, Jessell T M. Two critical periods of sonic hedgehog signaling required for the specification of motor neuron identity. *Cell.* 1996; 87:661-673.
2. Marigo V, Tabin C J. Regulation of patched by sonic hedgehog in the developing neural tube. *Proc Natl Acad Sci USA.* 1996; 93:9346-9351.
3. Levin M, Johnson R L, Stern C D, Kuehn M, Tabin C. A molecular pathway determining left-right asymmetry in chick embryogenesis. *Cell.* 1995; 82:803-814.
4. Wilson G N. Correlated heart/limb anomalies in mendelian syndromes provide evidence for a cardiomelic developmental field. *Am J Med Genet.* 1998; 76:297-305.
5. Dahmane N, Lee J, Robins P, Heller P, Ruiz i Altaba A. Activation of the transcription factor gli1 and the sonic hedgehog signalling pathway in skin tumours. *Nature.* 1997; 389:876-881.
6. Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M. Hedgehog is an early and late mediator of pancreatic cancer tumorigenesis. *Nature.* 2003; 425: 851-856.
7. Gianakopoulos P J, Skerjanc I S. Hedgehog signaling induces cardiomyogenesis in p19 cells. *J Biol Chem.* 2005; 280:21022-21028.
8. Lin L, Bu L, Cai C L, Zhang X, Evans S. Isl1 is upstream of sonic hedgehog in a pathway required for cardiac morphogenesis. *Dev Biol.* 2006; 295:756-763.
9. Lavine K J, Long F, Choi K, Smith C, Ornitz D M. Hedgehog signaling to distinct cell types differentially regulates coronary artery and vein development. *Development.* 2008; 135:3161-3171.
10. Goddeeris M M, Rho S, Petiet A, Davenport C L, Johnson G A, Meyers E N, Klingensmith J. Intracardiac septation requires hedgehog-dependent cellular contributions from outside the heart. *Development.* 2008; 135: 1887-1895.
11. Thomas N A, Koudijs M, van Eeden F J, Joyner A L, Yelon D. Hedgehog signaling plays a cell-autonomous role in maximizing cardiac developmental potential. *Development.* 2008; 135:3789-3799.
12. Kusano K F, Pola R, Murayama T, Curry C, Kawamoto A, Iwakura A, Shintani S, Ii M, Asai J, Tkebuchava T, Thorne T, Takenaka H, Aikawa R, Goukassian D, von Samson P, Hamada H, Yoon Y S, Silver M, Eaton E, Ma H, Heyd L, Kearney M, Munger W, Porter J A, Kishore R, Losordo D W. Sonic hedgehog myocardial gene therapy: Tissue repair through transient reconstitution of embryonic signaling. *Nat Med.* 2005; 11:1197-1204.
13. Pola R, Ling L E, Silver M, Corbley M J, Kearney M, Blake Pepinsky R, Shapiro R, Taylor F R, Baker D P, Asahara T, Isner J M. The morphogen sonic hedgehog is an indirect angiogenic agent upregulating two families of angiogenic growth factors. *Nat Med.* 2001; 7:706-711.
14. Lavine K J, Kovacs A, Ornitz D M. Hedgehog signaling is critical for maintenance of the adult coronary vasculature in mice. *J Clin Invest.* 2008; 118:2404-2414.
15. Ueda K, Takano H, Niitsuma Y, Hasegawa H, Uchiyama R, Oka T, Miyazaki M, Nakaya H, Komuro I. Sonic hedgehog is a critical mediator of erythropoietin-induced cardiac protection in mice. *J Clin Invest.* 2010; 120:2016-2029.
16. Agouni A, Mostefai H A, Porro C, Carusio N, Favre J, Richard V, Henrion D, Martinez M C, Andriantsitohaina R. Sonic hedgehog carried by microparticles corrects endothelial injury through nitric oxide release. *Faseb J.* 2007; 21:2735-2741.
17. Benameur T, Soleti R, Porro C, Andriantsitohaina R, Martinez M C. Microparticles carrying sonic hedgehog favor neovascularization through the activation of nitric oxide pathway in mice. *PLoS One.* 2010; 5:e12688.
18. Martinez M C, Larbret F, Zobairi F, Coulombe J, Debili N, Vainchenker W, Ruat M, Freyssinet J M. Transfer of differentiation signal by membrane microvesicles harboring hedgehog morphogens. *Blood.* 2006; 108:3012-3020.
Martinez M C, Tual-Chalot S, Leonetti D, Andriantsitohaina R. Microparticles: Targets and tools in cardiovascular disease. *Trends Pharmacol Sci.* 2011; 32:659-665.
Soleti R., Benameur T., Porro C., Panaro M. A., Andriantsitohaina R., Martinez M. C. Microparticles harboring Sonic Hedgehog promote angiogenesis through the up-regulation of adhesion proteins and pro-angiogenic factors. *Carcinogenesis* 2009; 30:580-588.
Soleti R, Lauret E, Andriantsitohaina R, Martinez M C. Internalization and induction of antioxidant messages by microvesicles contributes to the antiapoptotic effects on human endothelial cells. *Free Rad Biol Med* 2012; 53:2159-2170.
19. Riobo N A, Lu K, Ai X, Haines G M, Emerson C P, Jr. Phosphoinositide 3-kinase and akt are essential for sonic hedgehog signaling. *Proc Natl Acad Sci USA.* 2006; 103:4505-4510.
20. Mutoh A, Isshiki M, Fujita T. Aldosterone enhances ligand-stimulated nitric oxide production in endothelial cells. *Hypertens Res.* 2008; 31:1811-1820.
21. Cazorla O, Szilagyi S, Le Guennec J Y, Vassort G, Lacampagne A. Transmural stretch-dependent regulation of contractile properties in rat heart and its alteration after myocardial infarction. *Faseb J.* 2005; 19:88-90.
22. Cazorla O, Lucas A, Poirier F, Lacampagne A, Lezoualc'h F. The camp binding protein epac regulates cardiac myofilament function. *Proc Natl Acad Sci USA.* 2009; 106:14144-14149.
23. Pandit S V, Clark R B, Giles W R, Demir S S. A mathematical model of action potential heterogeneity in adult rat left ventricular myocytes. *Biophys J.* 2001; 81:3029-3051.
24. Marigo V, Davey R A, Zuo Y, Cunningham J M, Tabin C J. Biochemical evidence that patched is the hedgehog receptor. *Nature.* 1996; 384:176-179.

25. Denef N, Neubuser D, Perez L, Cohen S M. Hedgehog induces opposite changes in turnover and subcellular localization of patched and smoothened. *Cell.* 2000; 102:521-531.
26. Esposito G, Santana L F, Dilly K, Cruz J D, Mao L, Lederer W J, Rockman H A. Cellular and functional defects in a mouse model of heart failure. *Am J Physiol Heart Circ Physiol.* 2000; 279:H3101-3112.
27. Hare J M. Nitric oxide and excitation-contraction coupling. *J Mol Cell Cardiol.* 2003; 35:719-729.
28. Bouchard R A, Clark R B, Giles W R. Effects of action potential duration on excitation-contraction coupling in rat ventricular myocytes. Action potential voltage-clamp measurements. *Circ Res.* 1995; 76:790-801.
29. Chai Y, Lin Y F. Dual regulation of the atp-sensitive potassium channel by activation of cgmp-dependent protein kinase. *Pflugers Arch.* 2008; 456:897-915.
30. Chai Y, Lin Y F. Stimulation of neuronal katp channels by cgmp-dependent protein kinase: Involvement of ros and 5-hydroxydecanoate-sensitive factors in signal transduction. *Am J Physiol Cell Physiol.* 2010; 298:C875-892.
31. Galdino G S, Cortes S F, Duarte I D, Perez A C. Involvement of the nitric oxide/(c)gmp/k(atp) pathway in antinociception induced by exercise in rats. *Life Sci.* 2010; 86:505-509.
32. Tamargo J, Caballero R, Gomez R, Valenzuela C, Delpon E. Pharmacology of cardiac potassium channels. *Cardiovasc Res.* 2004; 62:9-33.
33. Taipale J, Chen J K, Cooper M K, Wang B, Mann R K, Milenkovic L, Scott M P, Beachy P A. Effects of oncogenic mutations in smoothened and patched can be reversed by cyclopamine. *Nature.* 2000; 406:1005-1009.
34. Chen J K, Taipale J, Cooper M K, Beachy P A. Inhibition of hedgehog signaling by direct binding of cyclopamine to smoothened. *Genes Dev.* 2002; 16:2743-2748.
35. Kojda G, Kottenberg K, Nix P, Schluter K D, Piper H M, Noack E. Low increase in cgmp induced by organic nitrates and nitrovasodilators improves contractile response of rat ventricular myocytes. *Circ Res.* 1996; 78:91-101.
36. Brady A J, Warren J B, Poole-Wilson P A, Williams T J, Harding S E. Nitric oxide attenuates cardiac myocyte contraction. *Am J Physiol.* 1993; 265:H176-182.
37. Ziolo M T, Katoh H, Bers D M. Positive and negative effects of nitric oxide on ca(2+) sparks: Influence of beta-adrenergic stimulation. *Am J Physiol Heart Circ Physiol.* 2001; 281:H2295-2303.
38. Layland J, Li J M, Shah A M. Role of cyclic gmp-dependent protein kinase in the contractile response to exogenous nitric oxide in rat cardiac myocytes. *J Physiol.* 2002; 540:457-467.
39. Paulus W J, Vantrimpont P J, Shah A M. Acute effects of nitric oxide on left ventricular relaxation and diastolic distensibility in humans. Assessment by bicoronary sodium nitroprusside infusion. *Circulation.* 1994; 89:2070-2078.
40. Gonzalez D R, Fernandez I C, Ordenes P P, Treuer A V, Eller G, Boric M P. Differential role of s-nitrosylation and the no-cgmp-pkg pathway in cardiac contractility. *Nitric Oxide.* 2008; 18:157-167.
41. Flagg T P, Enkvetchakul D, Koster J C, Nichols C G. Muscle katp channels: Recent insights to energy sensing and myoprotection. *Physiol Rev.* 2010; 90:799-829.
42. Zhang H, Flagg T P, Nichols C G. Cardiac sarcolemmal k(atp) channels: Latest twists in a questing tale! *J Mol Cell Cardiol.* 2010; 48:71-75.

SUPPLEMENTAL REFERENCES

1. Cazorla O, Szilagyi S, Le Guennec J Y, Vassort G, Lacampagne A. Transmural stretch-dependent regulation of contractile properties in rat heart and its alteration after myocardial infarction. *Faseb J.* 2005; 19:88-90.
2. Martinez M C, Larbret F, Zobairi F, Coulombe J, Debili N, Vainchenker W, Ruat M, Freyssinet J M. Transfer of differentiation signal by membrane microvesicles harboring hedgehog morphogens. *Blood.* 2006; 108:3012-3020.
3. Cazorla O, Lucas A, Poirier F, Lacampagne A, Lezoualc'h F. The camp binding protein epac regulates cardiac myofilament function. *Proc Natl Acad Sci USA.* 2009; 106:14144-14149.
4. Bondarenko V E, Szigeti G P, Bett G C, Kim S J, Rasmusson R L. Computer model of action potential of mouse ventricular myocytes. *Am J Physiol.* 2004; 287(3):H1378-H1403.
5. Gamy A, Kohl P, Hunter P J, Boyett M R, Noble D. One-dimensional rabbit sinoatrial node models: Benefits and limitations. *J Cardiovasc Electrophysiol.* 2003; 14:S121-132.

The invention claimed is:

1. A method for reducing infarct size and reperfusion arrhythmias in a patient in need thereof, said patient having had a myocardial infarction, comprising the steps of
   i) restoring blood supply in cardiac ischemic tissue of the patient, and
   ii) inducing cardioprotection by administering to the patient a therapeutically effective amount of a ligand of the sonic hedgehog signaling pathway,
   wherein the step of inducing cardioprotection causes a reduction in infarct size and reperfusion arrhythmias in the patient,
   wherein the ligand of the sonic hedgehog signaling pathway is a sonic hedgehog polypeptide comprising a signaling domain of a hedgehog polypeptide,
   and wherein the signaling domain of the hedgehog polypeptide comprises a sequence having at least 90% identity with a sequence ranging from an amino acid residue at position 1 to an amino acid residue at position 197 in SEQ ID NO:1.

2. The method of claim 1 wherein the sonic hedgehog polypeptide is a soluble polypeptide.

3. The method of claim 1 wherein the sonic hedgehog polypeptide comprises the sequence ranging from the amino acid residue at position 1 to the amino acid residue at position 197 in SEQ ID NO:1 or a function conservative variant of said sequence.

4. The method of claim 1 wherein the sonic hedgehog polypeptide is fused to a Fc portion of an antibody.

5. The method of claim 1 wherein the sonic hedgehog polypeptide is carried by a microparticle.

6. The method of claim 1 wherein steps i) and ii) are performed sequentially or concomitantly.

7. The method of claim 1 wherein the therapeutically effective amount of the ligand of the sonic hedgehog signaling pathway is administered prior to and/or at the time of reperfusion injury.

8. The method of claim 1 wherein the ligand of the sonic hedgehog signaling pathway is administered by infusion into the bloodstream.

9. The method of claim 1 wherein the ligand is capable of activating i) the Patched-Smoothened complex or ii) the ATP-dependent potassium current ($I_{KATP}$), in adult cardiomyocytes.

10. The method of claim 1, wherein the percentage of identity is at least 95%.

11. The method of claim 1, wherein the percentage of identity is at least 96%.

12. The method of claim 1, wherein the percentage of identity is at least 97%.

13. The method of claim 1, wherein the percentage of identity is at least 98%.

14. The method of claim 1, wherein the percentage of identity is at least 99%.

15. The method of claim 1, wherein the percentage of identity is 100%.

16. The method of claim 1, wherein the ligand of the sonic hedgehog signaling pathway is a function conservative variant of the sonic hedgehog polypeptide.

* * * * *